US008642652B2

(12) United States Patent
Dierker et al.

(10) Patent No.: US 8,642,652 B2
(45) Date of Patent: Feb. 4, 2014

(54) COSMETIC COMPOSITIONS CONTAINING ESTERS BASED ON 2-PROPYLHEPTANOL

(75) Inventors: Markus Dierker, Duesseldorf (DE); Catherine Weichold, Aachen (DE); Stefanie Althaus, Koeln (DE); Lars Zander, Rommerskirchen (DE); Daniela Prinz, Dormagen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1192 days.

(21) Appl. No.: 11/886,623

(22) PCT Filed: Mar. 9, 2006

(86) PCT No.: PCT/EP2006/002148
§ 371 (c)(1),
(2), (4) Date: Dec. 28, 2008

(87) PCT Pub. No.: WO2006/097235
PCT Pub. Date: Sep. 21, 2006

(65) Prior Publication Data
US 2009/0182046 A1 Jul. 16, 2009

(30) Foreign Application Priority Data

Mar. 17, 2005 (DE) .......................... 10 2005 012 300
Jun. 10, 2005 (EP) ..................................... 05012510

(51) Int. Cl.
*A01N 37/00* (2006.01)
*A01N 27/00* (2006.01)
*A61K 31/21* (2006.01)
*A61K 31/215* (2006.01)
*A61K 31/01* (2006.01)

(52) U.S. Cl.
USPC ............................ 514/529; 514/506; 514/762

(58) Field of Classification Search
None
See application file for complete search history.

(56) References Cited

U.S. PATENT DOCUMENTS 5,639,791 A * 6/1997 O'Lenick, Jr. ................. 514/552
5,840,943 A 11/1998 Ansmann et al.
6,491,927 B1 * 12/2002 Arnaud et al. ................ 424/401
6,610,869 B1 8/2003 Huebner et al.
2004/0014865 A1 1/2004 Keller et al.
2005/0019353 A1 1/2005 Prinz et al.
2005/0089497 A1 4/2005 Prinz et al.
2007/0027244 A1 2/2007 Schar et al.

FOREIGN PATENT DOCUMENTS

| DE | 1138756 | 10/1962 |
| DE | 19926671 | 12/2000 |
| DE | 10160681 | 6/2003 |
| DE | 10160682 | 6/2003 |
| DE | 10305562 | 8/2004 |
| DE | 10305562 A1 * | 8/2004 |
| EP | 0766661 | 8/1999 |
| JP | 7157615 | 6/1995 |
| JP | 07157615 | 6/1995 |
| JP | 7278056 | 10/1995 |
| JP | 2004/511618 | 4/2004 |
| WO | 0114309 | 3/2001 |

OTHER PUBLICATIONS

EPO Machine Translation of DE10305562 from http://translationportal.epo.org/emtp/translate/?ACTION=description-retrieval&COUNTRY=DE&FORMAT=docdb&KIND=A1&LOCALE=en_EP&NUMBER=10305562&OPS=ops.epo.org&TRG-LANG=en&ENGINE=google&SRCLANG=de.*
EPO Machine Translation of DE10305562, published Aug. 2004, translation accessed Dec. 29, 2011.*
Kirk-Othmer Encyclopedia of Chemical Technology, Third Edition, vol. 8, *John Wiley & Sons*, 1979, 3 pgs.
Machine Translation of DE 1138756, 3 pgs., (Original dated Oct. 31, 1962).
Kirk-Othmer: Encyclopedia of Chemical Technology. Third Edition vol. 8, p. 913, 1979.
International Search Report PCT/EP2006/002148 dated May 15, 2006.
Machine Translation of JP-07278056, 7 pgs. 1995.
Machine Translation of JP-7157615, 9 pgs. 1995.

* cited by examiner

*Primary Examiner* — James D Anderson
*Assistant Examiner* — Stephanie Springer
(74) *Attorney, Agent, or Firm* — Servilla Whitney LLC

(57) ABSTRACT

Esters of 2-propylheptanol with linear or branched, saturated or unsaturated $C_5$-$C_{36}$ carboxylic acids and $C_4$-$C_{36}$ dicarboxylic acids, compositions comprising these esters, and to the use of esters of 2-propylheptanol with linear or branched, saturated or unsaturated $C_5$-$C_{36}$-carboxylic acids and/or $C_4$-$C_{36}$-dicarboxylic acids in cosmetic and/or topical pharmaceutical preparations.

11 Claims, No Drawings

US 8,642,652 B2

COSMETIC COMPOSITIONS CONTAINING ESTERS BASED ON 2-PROPYLHEPTANOL

CROSS-REFERENCE TO RELATED APPLICATIONS

This application is a national phase filing under 35 U.S.C. §371 and claims priority to International Application No. PCT/EP2006/002148 which has an International filing date of Mar. 9, 2006, and which claims priority to German Application Number 10 2005 012 300.7, filed Mar. 17, 2005, and European Application Number 05012510.3, filed Jun. 10, 2005, the entire disclosures of which are hereby incorporated herein by reference.

BACKGROUND OF THE INVENTION

1. Field of the Invention

The present invention relates to esters of 2-propylheptanol, to the use of esters of 2-propylheptanol in cosmetic and/or pharmaceutical preparations, and to a process for the production of such esters.

2. Background and Related Art

Cosmetic hair and skin-care emulsions are expected by the consumer to satisfy a number of requirements. Apart from the cleansing and caring effects which determine the particular application, importance is attributed to such diverse parameters as the highest possible dermatological compatibility, good lipid-layer-enhancing properties, elegant appearance, optimal sensory impression and shelf life.

Besides a number of surfactants, cosmetic hair- and skincare preparations generally contain, above all, oil components and water. The oil components (emollients) used include, for example, hydrocarbons, ester oils and vegetable and animal oils/fats/waxes. In order to satisfy increasingly stringent market requirements in regard to sensory properties and optimal dermatological compatibility, new oil components and emulsifier mixtures are being continuously developed and tested. In particular, because of the importance of ester oils, including branched ester oils that impart a "lighter" skin feel in cosmetic products, ester oils are the subject of intensive research and new processes for their production are being continuously developed. The use of 2-methyl-1,3-propanediol monoesters is described, for example, in DE 101 60 681; the use of 2-methyl-1,3-propanediol diesters is described in DE 101 60 682.

The problem addressed by the present invention was to provide new ester oils, preferably liquid at 20° C. for cosmetic applications, which would have an improved profile in regard to their sensory properties (lightness, non-greasy skin feel, softness, spreadability, absorption, distribution behavior, oiliness) and which could be incorporated in a number of cosmetic formulations. Hydrolysis stability of these esters, their capacity for formulation at low pH values, their ability to be incorporated both in water-in-oil and in oil-in-water formulations, and their compatibility, in particular, with crystalline UV filters, pigments, antiperspirants, salts and silicones were also to be of significance. It has now surprisingly been found that esters of 2-propylheptanol (some of which, with their production methods have already been known from DE 103 05 562 (published United States Patent Application 2007/027244, Schar et al), but for the totally different and unrelated application as polymer additives, and from Japanese Patent 05070403 (Chisso Corporation), but for use as acrylic binders with improved low-temperature adhesiveness for engines) lead to sensorially-light products.

BRIEF SUMMARY OF THE INVENTION

The present invention relates to esters of 2-propylheptanol with linear or branched, saturated or unsaturated $C_5$-$C_{36}$ carboxylic acids and/or $C_4$-$C_{36}$ dicarboxylic acids, to compositions comprising these esters, as well as to the use of these esters in cosmetic and/or pharmaceutical preparations.

Surprisingly, esters propyl-branched in the alkyl chain are particularly suitable for cosmetic formulations, more particularly for formulations expected to impart a "light" skin feel. The esters may be incorporated particularly well in various formulations, including liquid mixtures that may be used as oil components or consistency factors according to chain length, branching and number of double bonds of these esters. According to the invention, a single 2-propylheptyl $C_5$-$C_{36}$-carboxylic acid ester or 2-propylheptyl $C_4$-$C_{36}$-dicarboxylic acid ester or a mixture of two or more thereof may be used in such formulations.

The present invention relates in particular to the use of esters of 2-propylheptanol with linear or branched, saturated or unsaturated $C_5$-$C_{36}$ carboxylic acids or $C_4$-$C_{36}$ dicarboxylic acids in cosmetic and/or pharmaceutical preparations for wetting or impregnating or coating utility and/or hygiene wipes used for cleaning and/or care of the body.

A preferred embodiment of the invention is characterized by the use of esters containing a total of 24 or fewer carbon atoms, preferably 22 or fewer carbon atoms.

Another preferred embodiment of the invention is the use of esters of 2-propylheptanol with carboxylic acids selected from $C_5$ to $C_{30}$, particularly $C_6$ to $C_{24}$, more particularly $C_6$ to $C_{22}$, still more particularly $C_6$ to $C_{18}$, most particularly $C_8$ to $C_{18}$, preferably $C_8$ to $C_{16}$, more preferably $C_8$ to $C_{12}$, and still more preferably $C_6$ to $C_{10}$ carboxylic acids or the use of 2-propylheptanol with dicarboxylic acids selected from $C_4$ to $C_{30}$, particularly $C_6$ to $C_{24}$, more particularly $C_6$ to $C_{22}$, still more particularly $C_6$ to $C_{18}$, most particularly $C_8$ to $C_{18}$, preferably $C_8$ to $C_{16}$, more preferably $C_8$ to $C_{12}$, and still more preferably $C_6$ to $C_{10}$ dicarboxylic acids in cosmetic and/or topical pharmaceutical applications.

According to the invention, esters of 2-propylheptanol with $C_5$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, or $C_{13}$ or $C_{14}$ carboxylic acids or $C_4$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, or $C_{13}$ or $C_{14}$ dicarboxylic acids are suitable for use in cosmetic and/or topical pharmaceutical applications.

A particularly preferred embodiment of the invention is characterized by the use of esters of 2-propylheptanol with $C_6$ to $C_{12}$-carboxylic acids and/or $C_6$ to $C_{12}$-dicarboxylic acids for such applications.

According to the invention, the use of esters of 2-propylheptanol with saturated carboxylic acids and/or esters of 2-propylheptanol with saturated dicarboxylic acids within the above ranges is preferred.

Also preferred is the use of esters of 2-propylheptanol with linear, unbranched carboxylic acids and/or esters of 2-propylheptanol with linear, unbranched dicarboxylic acids within the above ranges.

DETAILED DESCRIPTION OF THE INVENTION

The term "$C_X$ carboxylic acids" encompasses carboxylic acids with a total carbon number of x, i.e., for example, "$C_8$-carboxylic acids" encompasses all carboxylic acids which have a total carbon number of 8, such as, for example, n-octanoic acid, iso-octanoic acids or methylheptanoic acids. Correspondingly, the term "$C_X$ dicarboxylic acids" encompasses all acids containing 2 carboxy groups which have a total carbon number of x, so that, for example, "$C_4$-dicarboxylic acid" encompasses, inter alia, butanedioic acid (succinic acid) and also maleic acid and fumaric acid.

In the context of the present invention, the term "carboxylic acid" applies to "monocarboxylic acids".

The sensory testing of 2-propylheptyl caprylate and 2-propylheptyl caproate shows that these compounds demonstrate a significant improvement in sensory properties, particularly in regard to spreading, over known emollients (for example, various other ester oils or dialkyl carbonates).

According to the invention, esters of 2-propylheptanol with, for example (with the common names of the acids in brackets), n-butanoic acid, (butyric acid), 2-methylpropanoic acid (isobutyric acid), pentanoic acid (valeric acid), i-pentanoic acid, such as, for example, 2,2-dimethylpropanoic acid (pivalic acid, neopentanoic acid) and 3-methylbutanoic acid (isopentanoic acid, isovaleric acid), hexanoic acid (caproic acid), heptanoic acid, octanoic acid (caprylic acid), i-octanoic acid, such as, for examples 2-propylheptyl-2-ethylhexanoic acid ester in particular, but also 2-propylheptyl-3-ethylhexanoic acid ester, 2-propylheptyl-4-ethylhexanoic acid ester, 2-propylheptyl-5-ethylhexanoic acid ester and technical mixtures of branched octanoic acids which are marketed, for example, under the name of Cekanoic® C8 by ExxonMobil Chemical, nonanoic acid (pelargonic acid, nonylic acid), decanoic acid (capric acid), i-decanoic acids, such as, for example, trimethylheptanoic acid (neodecanoic acid, isodecanoic acid), and technical mixtures of branched decanoic acids which are marketed, for example, under the name of Cekanoic® C10 by ExxonMobil, undecanoic acid, undecenoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid, eicosanoic acid, docosanoic acid, tetracosanoic acid, hexacosanoic acid, dimer fatty acids ($C_{36}$, obtainable for example under the name of "Empol® 1062" from Cognis Corporation, Cincinnati, Ohio), tallow fatty acids, coconut fatty acids, palm fatty acid, ricinoleic acid, oleic acid, linoleic acid, linolenic acid, isostearic acid, iso-octanoic acid, isononanoic acid, isodecanoic acid, 2-ethylhexanaoic acid, 2-propylheptanoic acid, 2-butyloctanoic acid, 2-butyldecanoic acid, 2-hexyloctanoic acid, 2-hexyldecanoic acid, 2-hexyldodecanoic acid, 2-octyldecanoic acid, or dicarboxylic acids, such as, for example, fumaric acid, maleic acid, adipic acid, pimelic acid, suberic acid, azelaic acid, sebacic acid, are suitable. Also suitable are esters of 2-propylheptanol with Cekanoic® C8, Cekanoic® C9 (isononanoic acid: 3,5,5-trimethylhexanoic acid and 2,5,5-trimethylhexanoic acid) and Cekanoic® C10, which are carboxylic acid isomer mixtures.

The expression "esters of 2-propylheptanol with dicarboxylic acids" encompasses both diesters of dicarboxylic acids with 2-propylheptanol, i.e., for example, di-2-propylheptyl-n-octanedioic acid diester, and monoesters, such as 2-propylheptyl-n-octanedioic acid monoester, for example, and mixed esters in which one acid group of the dicarboxylic acid is esterified with 2-propylheptanol and the second acid group of the dicarboxylic acid is esterified with another alcohol. One embodiment of the invention is characterized by the use of mixed esters of dicarboxylic acids and 2-propylheptanol and another alcohol selected from the group consisting of 3-methyl-2-propylhexanol, 4-methyl-2-propylhexanol and 5-methyl-2-propylhexanol. In a preferred embodiment of the invention, the mixed esters are obtained by reaction of the corresponding dicarboxylic acid with a mixture of 2-propylheptanol, 3-methyl-2-propylhexanol, 4-methyl-2-propylhexanol and 5-methyl-2-propylhexanol. Another embodiment is characterized by the use of mixed esters of dicarboxylic acids and 2-propylheptanol and another alcohol with the general formula R—OH, where R is a linear or branched, saturated or unsaturated alkyl group containing 1 to 12 carbon atoms.

Still another embodiment is characterized by the use of mixed esters of dicarboxylic acids and 2-propylheptanol and another alcohol with the general formula R—OH, where R is a saturated, linear or branched alkyl group containing 1 to 12 carbon atoms.

A preferred embodiment is characterized by the use of mixed esters of dicarboxylic acids and 2-propylheptanol and another alcohol, the other alcohol being selected from the group consisting of methanol, ethanol, propanol, isopropanol, butanol, isobutanol, pentanol, hexanol, isohexanol, octanol, decanol and dodecanol.

In a preferred embodiment of the invention, diesters and mixed esters are used as the esters of 2-propylheptanol with $C_4$ to $C_{36}$ dicarboxylic acids.

The present invention also relates to esters of 2-propylheptanol with carboxylic acids selected from linear or branched, saturated or unsaturated $C_5$ to $C_{36}$ carboxylic acids. The invention encompasses both individual esters and mixtures of different esters.

A preferred embodiment of the invention are esters of 2-propylheptanol with linear or branched, saturated or unsaturated $C_5$ to $C_{30}$ carboxylic acids, particularly $C_6$ to $C_{24}$, more particularly $C_6$ to $C_{22}$, still more particularly $C_6$ to $C_{18}$, most particularly $C_8$ to $C_{18}$, preferably $C_8$ to $C_{16}$, more preferably $C_8$ to $C_{12}$, still more preferably $C_6$ to $C_{10}$ carboxylic acids.

According to the invention, esters of 2-propylheptanol with $C_5$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, and $C_{13}$ or $C_{14}$ carboxylic acids are preferred.

A particularly preferred embodiment of the invention are esters of 2-propylheptanol with $C_6$ to $C_{12}$ carboxylic acids.

According to the invention, esters of 2-propylheptanol with saturated carboxylic acids within the above ranges are preferred.

According to the invention, esters of 2-propylheptanol with linear, saturated carboxylic acids within the above ranges are particularly preferred.

The present invention encompasses esters of 2-propylheptanol with linear and/or branched carboxylic acids of the above ranges. One embodiment of the invention relates to esters of 2-propylheptanol with branched carboxylic acids. In the context of the invention, the term "i-acid" with x carbon atoms means any branched carboxylic acids which contain, in all, x carbon atoms, i.e., for example methyl, ethyl or propyl-branched, optionally multi-branched carboxylic acids. One particular embodiment is characterized by the use of the sub-group of—optionally repeatedly—methyl-branched carboxylic acids (=iso-acids).

The following esters are preferred: 2-propylheptyl-n-hexanoic acid ester, 2-propylheptyl-n-heptanoic acid ester, 2-propylheptyl-n-octanoic acid ester, 2-propylheptyl-n-nonanoic acid ester, 2-propylheptyl-n-decanoic acid ester, 2-propylheptyl-n-undecanoic acid ester, and 2-propylheptyl-n-dodecanoic acid ester.

The following esters are particularly preferred: 2-propylheptyl-n-hexanoic acid ester, 2-propylheptyl-n-octanoic acid ester, 2-propylheptyl-n-decanoic acid ester, and 2-propylheptyl-n-dodecanoic acid ester.

The following esters are also preferred: 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n-dodecanoic acid ester, and 2-propylheptyl-i-dodecanoic acid ester.

The following esters are also particularly preferred: 2-propylheptyl-n-hexanoic acid ester, 2-propylheptyl-i-hexanoic acid ester, 2-propylheptyl-n-n-octanoic acid ester, 2-propylheptyl-i-octanoic acid ester, 2-propylheptyl-n-decanoic acid ester, 2-propylheptyl-i-decanoic acid ester, 2-propylheptyl-n-dodecanoic acid ester, and 2-propylheptyl-i-dodecanoic acid ester.

The present invention also relates to compositions containing an ester of 2-propylheptanol with a $C_5$ to $C_{36}$-carboxylic acid or a $C_4$ to $C_{36}$-dicarboxylic acid and at least one other ester of the same respective acid with an alcohol selected from the group consisting of 3-methyl-2-propylhexanol, 4-methyl-2-propylhexanol and 5-methyl-2-propylhexanol.

In a preferred embodiment of the invention, these compositions contain
80 to 99.99% by weight of the 2-propylheptyl ester and
0.01 to 20% by weight of the methyl-2-propylhexyl ester
with the carboxylic or dicarboxylic acid within the ranges above that is desired in the final molecule.

The present invention also relates to 2-propylheptyl-n-butanoic acid ester.

The present invention also relates to compositions containing 2-propylheptyl-n-butanoic acid ester and at least one member from the group consisting of 3-methyl-2-propylhexyl-n-butanoic acid ester, 4-methyl-2-propylhexyl-n-butanoic acid ester, 5-methyl-2-propylhexyl-n-butanoic acid ester and mixtures of two or more thereof.

The present invention also relates to 2-propylheptyl-i-butanoic acid ester.

The present invention also relates to compositions containing 2-propylheptyl-i-butanoic acid ester and at least one member from the group consisting of 3-methyl-2-propylhexyl-i-butanoic acid ester, 4-methyl-2-propylhexyl-i-butanoic acid ester, 5-methyl-2-propylhexyl-i-butanoic acid ester and mixtures of two or more thereof.

The present invention also relates to 2-propylheptyl-n-pentanoic acid ester.

The present invention also relates to compositions containing 2-propylheptyl-n-pentanoic acid ester and at least one member from the group consisting of 3-methyl-2-propylhexyl-n-pentanoic acid ester, 4-methyl-2-propylhexyl-n-pentanoic acid ester, 5-methyl-2-propylhexyl-n-pentanoic acid ester and mixtures of two or more thereof.

The present invention also relates to 2-propylheptyl-i-pentanoic acid ester.

The present invention also relates to compositions containing 2-propylheptyl-i-pentanoic acid ester and at least one member from the group consisting of 3-methyl-2-propylhexyl-i-pentanoic acid ester, 4-methyl-2-propylhexyl-i-pentanoic acid ester, 5-methyl-2-propylhexyl-i-pentanoic acid ester and mixtures of two or more thereof.

The present invention also relates to 2-propylheptyl-n-hexanoic acid ester.

The present invention also relates to compositions containing 2-propylheptyl-n-hexanoic acid ester and at least one member from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof.

The present invention also relates to 2-propylheptyl-i-hexanoic acid ester.

The present invention also relates to compositions containing 2-propylheptyl-i-hexanoic acid ester and at least one member from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof.

The present invention also relates to 2-propylheptyl-n-heptanoic acid ester.

The present invention also relates to compositions containing 2-propylheptyl-n-heptanoic acid ester and at least one member from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof.

The present invention also relates to 2-propylheptyl-i-heptanoic acid ester.

The present invention also relates to compositions containing 2-propylheptyl-i-heptanoic acid ester and at least one member from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures of two or more thereof.

The present invention also relates to 2-propylheptyl-n-octanoic acid ester.

The present invention also relates to compositions containing 2-propylheptyl-n-octanoic acid ester and at least one member from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof.

The present invention also relates to 2-propylheptyl-i-octanoic acid ester.

The present invention also relates to compositions containing 2-propylheptyl-i-octanoic acid ester and at least one member from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof.

The present invention also relates to 2-propylheptyl-n-nonanoic acid ester.

The present invention also relates to compositions containing 2-propylheptyl-n-nonanoic acid ester and at least one member from the group consisting of 3-methyl-2-propylhexyl-n-nonanoic acid ester, 4-methyl-2-propylhexyl-n-nonanoic acid ester, 5-methyl-2-propylhexyl-n-nonanoic acid ester and mixtures of two or more thereof.

The present invention also relates to 2-propylheptyl-i-nonanoic acid ester.

The present invention also relates to compositions containing 2-propylheptyl-i-nonanoic acid ester and at least one member from the group consisting of 3-methyl-2-propylhexyl-i-nonanoic acid ester, 4-methyl-2-propylhexyl-i-nonanoic acid ester, 5-methyl-2-propylhexyl-i-nonanoic acid ester and mixtures of two or more thereof.

The present invention also relates to 2-propylheptyl-n-decanoic acid ester.

The present invention also relates to compositions containing 2-propylheptyl-n-decanoic acid ester and at least one member from the group consisting of 3-methyl-2-propylhexyl-n-decanoic acid ester, 4-methyl-2-propylhexyl-n-decanoic acid ester, 5-methyl-2-propylhexyl-n-decanoic acid ester and mixtures of two or more thereof.

The present invention also relates to 2-propylheptyl-i-decanoic acid ester.

The present invention also relates to compositions containing 2-propylheptyl-i-decanoic acid ester and at least one member from the group consisting of 3-methyl-2-propylhexyl-i-decanoic acid ester, 4-methyl-2-propylhexyl-i-decanoic acid ester, 5-methyl-2-propylhexyl-i-decanoic acid ester and mixtures of two or more thereof.

The present invention also relates to 2-propylheptyl-n-undecanoic acid ester.

The present invention also relates to compositions containing 2-propylheptyl-n-undecanoic acid ester and at least one member from the group consisting of 3-methyl-2-propylhexyl-n-undecanoic acid ester, 4-methyl-2-propylhexyl-n-undecanoic acid ester, 5-methyl-2-propylhexyl-n-undecanoic acid ester and mixtures of two or more thereof.

The present invention also relates to 2-propylheptyl-i-undecanoic acid ester.

The present invention also relates to compositions containing 2-propylheptyl-i-undecanoic acid ester and at least one member from the group consisting of 3-methyl-2-propylhexyl-i-undecanoic acid ester, 4-methyl-2-propylhexyl-i-undecanoic acid ester, 5-methyl-2-propylhexyl-i-undecanoic acid ester and mixtures of two or more thereof.

The present invention also relates to 2-propylheptyl-n-undecenoic acid ester.

The present invention also relates to compositions containing 2-propylheptyl-n-undecenoic acid ester and at least one member from the group consisting of 3-methyl-2-propylhexyl-n-undecenoic acid ester, 4-methyl-2-propylhexyl-n-undecenoic acid ester, 5-methyl-2-propylhexyl-n-undecenoic acid ester and mixtures of two or more thereof.

The present invention also relates to 2-propylheptyl-i-undecenoic acid ester.

The present invention also relates to compositions containing 2-propylheptyl-i-undecenoic acid ester and at least one member from the group consisting of 3-methyl-2-propylhexyl-i-undecenoic acid ester, 4-methyl-2-propylhexyl-i-undecenoic acid ester, 5-methyl-2-propylhexyl-i-undecenoic acid ester and mixtures of two or more thereof.

The present invention also relates to 2-propylheptyl-n-dodecanoic acid ester.

The present invention also relates to compositions containing 2-propylheptyl-n-dodecanoic acid ester and at least one member from the group consisting of 3-methyl-2-propylhexyl-n-dodecanoic acid ester, 4-methyl-2-propylhexyl-n-dodecanoic acid ester, 5-methyl-2-propylhexyl-n-dodecanoic acid ester and mixtures of two or more thereof.

The present invention also relates to 2-propylheptyl-i-dodecanoic acid ester.

The present invention also relates to compositions containing 2-propylheptyl-i-dodecanoic acid ester and at least one member from the group consisting of 3-methyl-2-propylhexyl-i-dodecanoic acid ester, 4-methyl-2-propylhexyl-i-dodecanoic acid ester, 5-methyl-2-propylhexyl-i-dodecanoic acid ester and mixtures of two or more thereof.

It has surprisingly been found that 2-propylheptyl-n-butanoic acid ester, 2-propylheptyl-i-butanoic acid ester, 2-propylheptyl-n-pentanoic acid ester, 2-propylheptyl-i-pentanoic acid ester, 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n-undecenoic acid ester, 2-propylheptyl-i-undecenoic acid ester, 2-propylheptyl-n-dodecanoic acid ester, and 2-propylheptyl-i-dodecanoic acid ester, and compositions comprising 2-propylheptyl-n-butanoic acid ester and at least one member selected from the group consisting of 3-methyl-2-propylhexyl-n-butanoic acid ester, 4-methyl-2-propylhexyl-n-butanoic acid ester, 5-methyl-2-propylhexyl-n-butanoic acid ester and mixtures of two or more thereof; compositions comprising 2-propylheptyl-i-butanoic acid ester and at least one member selected from the group consisting of 3-methyl-2-propylhexyl-i-butanoic acid ester, 4-methyl-2-propylhexyl-i-butanoic acid ester, 5-methyl-2-propylhexyl-i-butanoic acid ester and mixtures of two or more thereof; compositions containing 2-propylheptyl-n-pentanoic acid ester and at least one member selected from the group consisting of 3-methyl-2-propylhexyl-n-pentanoic acid ester, 4-methyl-2-propylhexyl-n-pentanoic acid ester, 5-methyl-2-propylhexyl-n-pentanoic acid ester and mixtures of two or more thereof; compositions comprising 2-propylheptyl-i-pentanoic acid ester and at least one member selected from the group consisting of 3-methyl-2-propylhexyl-i-pentanoic acid ester, 4-methyl-2-propylhexyl-i-pentanoic acid ester, 5-methyl-2-propylhexyl-i-pentanoic acid ester and mixtures of two or more thereof; compositions comprising 2-propylheptyl-n-hexanoic acid ester and at least one member selected from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof; compositions comprising 2-propylheptyl-i-hexanoic acid ester and at least one member selected from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof; compositions comprising 2-propylheptyl-n-heptanoic acid ester and at least one member selected from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof; compositions comprising 2-propylheptyl-i-heptanoic acid ester and at least one member selected from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures of two or more thereof; compositions comprising 2-propylheptyl-n-octanoic acid ester and at least one member selected from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof; compositions comprising 2-propylheptyl-i-octanoic acid ester and at least one member selected from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof; compositions comprising 2-propylheptyl-n-nonanoic acid ester and at least one member selected from the group consisting of 3-methyl-2-propylhexyl-n-nonanoic acid ester, 4-methyl-2-propylhexyl-n-nonanoic acid ester, 5-methyl-2-propylhexyl-n-nonanoic acid ester and mixtures of two or more thereof; compositions comprising 2-propylheptyl-i-nonanoic acid ester and at least one member selected from the group consisting of 3-methyl-2-propylhexyl-i-nonanoic acid ester, 4-methyl-2-propylhexyl-i-nonanoic acid ester, 5-methyl-2-propylhexyl-i-nonanoic acid ester and mixtures of two or more thereof; compositions comprising 2-propylheptyl-n-decanoic acid ester and at least one member selected from the group consisting of 3-methyl-2-propylhexyl-n-decanoic acid ester, 4-methyl-2-propylhexyl-n-decanoic acid ester, 5-methyl-2-propylhexyl-n-decanoic acid ester and mixtures of two or more thereof; compositions comprising 2-propylheptyl-i-decanoic acid ester and at least one member selected from the group consisting of 3-methyl-2-propylhexyl-i-decanoic acid ester, 4-methyl-2-propylhexyl-i-decanoic acid ester, 5-methyl-2-propylhexyl-i-decanoic acid ester and mixtures of two or more thereof; compositions comprising 2-propylheptyl-n-undecanoic acid ester and at least one member selected from the group consisting of 3-methyl-2-propylhexyl-n-undecanoic acid ester, 4-methyl-2-propylhexyl-n-undecanoic acid ester, 5-methyl-2-propylhexyl-n-undecanoic acid ester and mixtures of two or more thereof; compositions comprising 2-propylheptyl-i-undecanoic acid ester and at least one member selected from the group consisting of 3-methyl-2-propylhexyl-i-undecanoic acid ester, 4-methyl-2-propylhexyl-i-undecanoic acid ester, 5-methyl-2-propylhexyl-i-undecanoic acid ester and mixtures of two or more thereof; compositions comprising 2-propylheptyl-n-undecenoic acid ester and at least one member selected from the group consisting of 3-methyl-2-propylhexyl-n-undecenoic acid ester, 4-methyl-2-propylhexyl-n-undecenoic acid ester, 5-methyl-2-propylhexyl-n-undecenoic acid ester, and mixtures of two or more thereof; compositions comprising 2-propylheptyl-i-undecenoic acid ester and at least one member selected from the group consisting of 3-methyl-2-propylhexyl-i-undecenoic acid ester, 4-methyl-2-propylhexyl-i-undecenoic acid ester, 5-methyl-2-propylhexyl-i-undecenoic acid ester, and mixtures of two or more thereof; compositions comprising 2-propylheptyl-n-dodecanoic acid ester and at least one member selected from the group consisting of 3-methyl-2-propylhexyl-n-dodecanoic acid ester, 4-methyl-2-propylhexyl-n-dodecanoic acid ester, 5-methyl-2-propylhexyl-n-dodecanoic acid ester and mixtures of two or more thereof; and compositions comprising 2-propylheptyl-i-dodecanoic acid ester and at least one member selected from the group consisting of 3-methyl-2-propylhexyl-i-dodecanoic acid ester, 4-methyl-2-propylhexyl-i-dodecanoic acid ester, 5-methyl-2-propylhexyl-i-dodecanoic acid ester and mixtures of two or more thereof are particularly suitable for use in cosmetic and/or pharmaceutical preparations. Accordingly, the present invention also relates to the use of one or more of these esters or one or more of these compositions in cosmetic and/or pharmaceutical preparations.

The present invention also relates to 2-propylheptyl-n-tridecanoic acid ester.

The present invention also relates to compositions containing 2-propylheptyl-n-tridecanoic acid ester and at least one member from the group consisting of 3-methyl-2-propylhexyl-n-tridecanoic acid ester, 4-methyl-2-propylhexyl-n-tridecanoic acid ester, 5-methyl-2-propylhexyl-n-tridecanoic acid ester and mixtures of two or more thereof.

The present invention also relates to 2-propylheptyl-i-tridecanoic acid ester.

The present invention also relates to compositions containing 2-propylheptyl-i-tridecanoic acid ester and at least one member from the group consisting of 3-methyl-2-propylhexyl-i-tridecanoic acid ester, 4-methyl-2-propylhexyl-i-tridecanoic acid ester, 5-methyl-2-propylhexyl-i-tridecanoic acid ester and mixtures of two or more thereof.

The present invention also relates to 2-propylheptyl-n-tetradecanoic acid ester.

The present invention also relates to compositions containing 2-propylheptyl-n-tetradecanoic acid ester and at least one member from the group consisting of 3-methyl-2-propylhexyl-n-tetradecanoic acid ester, 4-methyl-2-propylhexyl-n-tetradecanoic acid ester, 5-methyl-2-propylhexyl-n-tetradecanoic acid ester and mixtures of two or more thereof.

The present invention also relates to 2-propylheptyl-i-tetradecanoic acid ester.

The present invention also relates to compositions containing 2-propylheptyl-i-tetradecanoic acid ester and at least one member from the group consisting of 3-methyl-2-propylhexyl-i-tetradecanoic acid ester, 4-methyl-2-propylhexyl-i-tetradecanoic acid ester, 5-methyl-2-propylhexyl-i-tetradecanoic acid ester and mixtures of two or more thereof.

The present invention also relates to 2-propylheptyl-n-pentadecanoic acid ester.

The present invention also relates to compositions containing 2-propylheptyl-n-pentadecanoic acid ester and at least one member from the group consisting of 3-methyl-2-propylhexyl-n-pentadecanoic acid ester, 4-methyl-2-propylhexyl-n-pentadecanoic acid ester, 5-methyl-2-propylhexyl-n-pentadecanoic acid ester and mixtures of two or more thereof.

The present invention also relates to 2-propylheptyl-i-pentadecanoic acid ester.

The present invention also relates to compositions containing 2-propylheptyl-i-pentadecanoic acid ester and at least one member from the group consisting of 3-methyl-2-propylhexyl-i-pentadecanoic acid ester, 4-methyl-2-propylhexyl-i-pentadecanoic acid ester, 5-methyl-2-propylhexyl-i-pentadecanoic acid ester and mixtures of two or more thereof.

The present invention also relates to 2-propylheptyl-n-hexadecanoic acid ester.

The present invention also relates to compositions containing 2-propylheptyl-n-hexadecanoic acid ester and at least one member from the group consisting of 3-methyl-2-propylhexyl-n-hexadecanoic acid ester, 4-methyl-2-propylhexyl-n-hexadecanoic acid ester, 5-methyl-2-propylhexyl-n-hexadecanoic acid ester and mixtures of two or more thereof.

The present invention also relates to 2-propylheptyl-i-hexadecanoic acid ester.

The present invention also relates to compositions containing 2-propylheptyl-i-hexadecanoic acid ester and at least one member from the group consisting of 3-methyl-2-propylhexyl-i-hexadecanoic acid ester, 4-methyl-2-propylhexyl-i-hexadecanoic acid ester, 5-methyl-2-propylhexyl-i-hexadecanoic acid ester and mixtures of two or more thereof.

The present invention also relates to 2-propylheptyl-n-heptadecanoic acid ester.

The present invention also relates to compositions containing 2-propylheptyl-n-heptadecanoic acid ester and at least one member from the group consisting of 3-methyl-2-propylhexyl-n-heptadecanoic acid ester, 4-methyl-2-propylhexyl-n-heptadecanoic acid ester, 5-methyl-2-propylhexyl-n-heptadecanoic acid ester and mixtures of two or more thereof.

The present invention also relates to 2-propylheptyl-i-heptadecanoic acid ester.

The present invention also relates to compositions containing 2-propylheptyl-i-heptadecanoic acid ester and at least one member from the group consisting of 3-methyl-2-propylhexyl-i-heptadecanoic acid ester, 4-methyl-2-propylhexyl-i-heptadecanoic acid ester, 5-methyl-2-propylhexyl-i-heptadecanoic acid ester and mixtures of two or more thereof.

The present invention also relates to 2-propylheptyl-n-octadecanoic acid ester.

The present invention also relates to compositions containing 2-propylheptyl-n-octadecanoic acid ester and at least one member from the group consisting of 3-methyl-2-propylhexyl-n-octadecanoic acid ester, 4-methyl-2-propylhexyl-n-octadecanoic acid ester, 5-methyl-2-propylhexyl-n-octadecanoic acid ester and mixtures of two or more thereof.

The present invention also relates to 2-propylheptyl-i-octadecanoic acid ester.

The present invention also relates to compositions containing 2-propylheptyl-i-octadecanoic acid ester and at least one member from the group consisting of 3-methyl-2-propylhexyl-i-octadecanoic acid ester, 4-methyl-2-propylhexyl-i-octadecanoic acid ester, 5-methyl-2-propylhexyl-i-octadecanoic acid ester and mixtures of two or more thereof.

The present invention also relates to 2-propylheptyl-cis-9-octadecenoic acid ester (=ester of oleic acid).

The present invention also relates to compositions containing 2-propylheptyl-cis-9-octadecenoic acid ester and at least one member from the group consisting of 3-methyl-2-propylhexyl-cis-9-octadecenoic acid ester, 4-methyl-2-propylhexyl-cis-9-octadecenoic acid ester, 5-methyl-2-propylhexyl-cis-9-octadecenoic acid ester and mixtures of two or more thereof.

The present invention also relates to 2-propylheptyl-(Z,Z)-9,12-octadecadienoic acid ester (=ester of linoleic acid).

The present invention also relates to compositions containing 2-propylheptyl-(Z,Z)-9,12-octadecadienoic acid ester and at least one member from the group consisting of 3-methyl-2-propylheptyl-(Z,Z)-9,12-octadecadienoic acid ester, 4-methyl-2-propylhexyl-(Z,Z)-9,12-octadecadienoic acid ester, 5-methyl-2-propylhexyl-(Z,Z)-9,12-octadecadienoic acid ester and mixtures of two or more thereof.

The present invention also relates to 2-propylheptyl-(all-Z)-9,12,15-octadecatrienoic acid ester (=ester of linolenic acid).

The present invention also relates to compositions containing 2-propylheptyl-(all-Z)-9,12,15-octadecatrienoic acid ester and at least one member from the group consisting of 3-methyl-2-propylheptyl-(all-Z)-9,12,15-octadecatrienoic acid ester, 4-methyl-2-propylhexyl-(all-Z)-9,12,15-octadecatrienoic acid ester, 5-methyl-2-propylhexyl-(all-Z)-9,12,15-octadecatrienoic acid ester and mixtures of two or more thereof.

The present invention also relates to 2-propylheptyl-n-nonadecanoic acid ester.

The present invention also relates to compositions containing 2-propylheptyl-n-nonadecanoic acid ester and at least one member from the group consisting of 3-methyl-2-propylhexyl-n-nonadecanoic acid ester, 4-methyl-2-propylhexyl-n-nonadecanoic acid ester, 5-methyl-2-propylhexyl-n-nonadecanoic acid ester and mixtures of two or more thereof.

The present invention also relates to 2-propylheptyl-i-nonadecanoic acid ester.

The present invention also relates to compositions containing 2-propylheptyl-i-nonadecanoic acid ester and at least one member from the group consisting of 3-methyl-2-propylhexyl-i-nonadecanoic acid ester, 4-methyl-2-propylhexyl-i-nonadecanoic acid ester, 5-methyl-2-propylhexyl-i-nonadecanoic acid ester and mixtures of two or more thereof.

The present invention also relates to 2-propylheptyl-n-eicosanoic acid ester.

The present invention also relates to compositions containing 2-propylheptyl-n-eicosanoic acid ester and at least one member from the group consisting of 3-methyl-2-propylhexyl-n-eicosanoic acid ester, 4-methyl-2-propylhexyl-n-eicosanoic acid ester, 5-methyl-2-propylhexyl-n-eicosanoic acid ester and mixtures of two or more thereof.

The present invention also relates to 2-propylheptyl-i-eicosanoic acid ester.

The present invention also relates to compositions containing 2-propylheptyl-i-eicosanoic acid ester and at least one member from the group consisting of 3-methyl-2-propylhexyl-i-eicosanoic acid ester, 4-methyl-2-propylhexyl-i-eicosanoic acid ester, 5-methyl-2-propylhexyl-i-eicosanoic acid ester and mixtures of two or more thereof.

The present invention also relates to 2-propylheptyl-n-docosanoic acid ester.

The present invention also relates to compositions containing 2-propylheptyl-n-docosanoic acid ester and at least one member from the group consisting of 3-methyl-2-propylhexyl-n-docosanoic acid ester, 4-methyl-2-propylhexyl-n-docosanoic acid ester, 5-methyl-2-propylhexyl-n-docosanoic acid ester and mixtures of two or more thereof.

The present invention also relates to 2-propylheptyl-i-docosanoic acid ester.

The present invention also relates to compositions containing 2-propylheptyl-i-docosanoic acid ester and at least one member from the group consisting of 3-methyl-2-propylhexyl-i-docosanoic acid ester, 4-methyl-2-propylhexyl-i-docosanoic acid ester, 5-methyl-2-propylhexyl-i-docosanoic acid ester and mixtures of two or more thereof.

The present invention also relates to 2-propylheptyl-n-tetracosanoic acid ester.

The present invention also relates to compositions containing 2-propylheptyl-n-tetracosanoic acid ester and at least one member from the group consisting of 3-methyl-2-propylhexyl-n-tetracosanoic acid ester, 4-methyl-2-propylhexyl-n-tetracosanoic acid ester, 5-methyl-2-propylhexyl-n-tetracosanoic acid ester and mixtures of two or more thereof.

The present invention also relates to 2-propylheptyl-i-tetracosanoic acid ester.

The present invention also relates to compositions containing 2-propylheptyl-i-tetracosanoic acid ester and at least one member from the group consisting of 3-methyl-2-propylhexyl-i-tetracosanoic acid ester, 4-methyl-2-propylhexyl-i-tetracosanoic acid ester, 5-methyl-2-propylhexyl-i-tetracosanoic acid ester and mixtures of two or more thereof.

The present invention also relates to 2-propylheptyl-n-hexacosanoic acid ester.

The present invention also relates to compositions containing 2-propylheptyl-n-hexacosanoic acid ester and at least one member from the group consisting of 3-methyl-2-propylhexyl-n-hexacosanoic acid ester, 4-methyl-2-propylhexyl-n-hexacosanoic acid ester, 5-methyl-2-propylhexyl-n-hexacosanoic acid ester and mixtures of two or more thereof.

The present invention also relates to 2-propylheptyl-i-hexacosanoic acid ester.

The present invention also relates to compositions containing 2-propylheptyl-i-hexacosanoic acid ester and at least one member from the group consisting of 3-methyl-2-propylhexyl-i-hexacosanoic acid ester, 4-methyl-2-propylhexyl-i-hexacosanoic acid ester, 5-methyl-2-propylhexyl-i-hexacosanoic acid ester and mixtures of two or more thereof.

The present invention also relates to a process for the production of the esters according to the invention in which a mixture containing 2-propylheptanol and the $C_5$-$C_{36}$ carboxylic or $C_4$-$C_{36}$ dicarboxylic acid that is desired in the final molecule is reacted.

The present invention also relates to a process for the production of 2-propylheptyl-n-butanoic acid ester, 2-propylheptyl-i-butanoic acid ester, 2-propylheptyl-n-pentanoic acid ester, 2-propylheptyl-i-pentanoic acid ester, 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n- undecenoic acid ester, 2-propylheptyl-i-undecenoic acid ester, 2-propylheptyl-n-dodecanoic acid ester, and 2-propylheptyl-i-dodecanoic acid ester, in which a mixture containing 2-propylheptanol and the acid that is desired in the final molecule (i.e., n-butanoic acid, i-butanoic acid, n-pentanoic acid, i-pentanoic acid, n-hexanoic acid, i-hexanoic acid, n-heptanoic acid, i-heptanoic acid, n-octanoic acid, i-octanoic acid, n-nonanoic acid, i-nonanoic acid, n-decanoic acid, i-decanoic acid, n-undecanoic acid, i-undecanoic acid, n-undecenoic acid, i-undecenoic acid, n-dodecanoic acid or i-dodecanoic acid) is reacted.

The process according to the invention also encompasses the production of ester mixtures, in which 2-propylheptanol is reacted together with the mixtures of acids desired in the final compositions.

The process according to the invention also encompasses the production of the compositions comprising 2-propylheptyl-n-butanoic acid ester and at least one member selected from the group consisting of 3-methyl-2-propylhexyl-n-butanoic acid ester, 4-methyl-2-propylhexyl-n-butanoic acid ester, 5-methyl-2-propylhexyl-n-butanoic acid ester and mixtures of two or more thereof; compositions comprising 2-propylheptyl-i-butanoic acid ester and at least one member selected from the group consisting of 3-methyl-2-propylhexyl-i-butanoic acid ester, 4-methyl-2-propylhexyl-i-butanoic acid ester, 5-methyl-2-propylhexyl-i-butanoic acid ester and mixtures of two or more thereof; compositions containing 2-propylheptyl-n-pentanoic acid ester and at least one member selected from the group consisting of 3-methyl-2-propylhexyl-n-pentanoic acid ester, 4-methyl-2-propylhexyl-n-pentanoic acid ester, 5-methyl-2-propylhexyl-n-pentanoic acid ester and mixtures of two or more thereof; compositions comprising 2-propylheptyl-i-pentanoic acid ester and at least one member selected from the group consisting of 3-methyl-2-propylhexyl-i-pentanoic acid ester, 4-methyl-2-propylhexyl-i-pentanoic acid ester, 5-methyl-2-propylhexyl-i-pentanoic acid ester and mixtures of two or more thereof; compositions comprising 2-propylheptyl-n-hexanoic acid ester and at least one member selected from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof; compositions comprising 2-propylheptyl-i-hexanoic acid ester and at least one member selected from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof; compositions comprising 2-propylheptyl-n-heptanoic acid ester and at least one member selected from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof; compositions comprising 2-propylheptyl-i-heptanoic acid ester and at least one member selected from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures of two or more thereof; compositions comprising 2-propylheptyl-n-octanoic acid ester and at least one member selected from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof; compositions comprising 2-propylheptyl-i-octanoic acid ester and at least one member selected from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof; compositions comprising 2-propylheptyl-n-nonanoic acid ester and at least one member selected from the group consisting of 3-methyl-2-propylhexyl-n-nonanoic acid ester, 4-methyl-2-propylhexyl-n-nonanoic acid ester, 5-methyl-2-propylhexyl-n-nonanoic acid ester and mixtures of two or more thereof; compositions comprising 2-propylheptyl-i-nonanoic acid ester and at least one member selected from the group consisting of 3-methyl-2-propylhexyl-i-nonanoic acid ester, 4-methyl-2-propylhexyl-i-nonanoic acid ester, 5-methyl-2-propylhexyl-i-nonanoic acid ester and mixtures of two or more thereof; compositions comprising 2-propylheptyl-n-decanoic acid ester and at least one member selected from the group consisting of 3-methyl-2-propylhexyl-n-decanoic acid ester, 4-methyl-2-propylhexyl-n-decanoic acid ester, 5-methyl-2-propylhexyl-n-decanoic acid ester and mixtures of two or more thereof; compositions comprising 2-propylheptyl-i-decanoic acid ester and at least one member selected from the group consisting of 3-methyl-2-propylhexyl-i-decanoic acid ester, 4-methyl-2-propylhexyl-i-decanoic acid ester, 5-methyl-2-propylhexyl-i-decanoic acid ester and mixtures of two or more thereof; compositions comprising 2-propylheptyl-n-undecanoic acid ester and at least one member selected from the group consisting of 3-methyl-2-propylhexyl-n-undecanoic acid ester, 4-methyl-2-propylhexyl-n-undecanoic acid ester, 5-methyl-2-propylhexyl-n-undecanoic acid ester and mixtures of two or more thereof; compositions comprising 2-propylheptyl-i-undecanoic acid ester and at least one member selected from the group consisting of 3-methyl-2-propylhexyl-i-undecanoic acid ester, 4-methyl-2-propylhexyl-i-undecanoic acid ester, 5-methyl-2-propylhexyl-i-undecanoic acid ester and mixtures of two or more thereof; compositions comprising 2-propylheptyl-n-undecenoic acid ester and at least one member selected from the group consisting of 3-methyl-2-propylhexyl-n-undecenoic acid ester, 4-methyl-2-propylhexyl-n-undecenoic acid ester, 5-methyl-2-propylhexyl-n-undecenoic acid ester, and mixtures of two or more thereof; compositions comprising 2-propylheptyl-i-undecenoic acid ester and at least one member selected from the group consisting of 3-methyl-2-propylhexyl-i-undecenoic acid ester, 4-methyl-2-propylhexyl-i-undecenoic acid ester, 5-methyl-2-propylhexyl-i-undecenoic acid ester, and mixtures of two or more thereof; compositions comprising 2-propylheptyl-n-dodecanoic acid ester and at least one member selected from the group consisting of 3-methyl-2-propylhexyl-n-dodecanoic acid ester, 4-methyl-2-propylhexyl-n-dodecanoic acid ester, 5-methyl-2-propylhexyl-n-dodecanoic acid ester and mixtures of two or more thereof; and compositions comprising 2-propylheptyl-i-dodecanoic acid ester and at least one member selected from the group consisting of 3-methyl-2-propylhexyl-i-dodecanoic acid ester, 4-methyl-2-propylhexyl-i-dodecanoic acid ester, 5-methyl-2-propylhexyl-i-dodecanoic acid ester and mixtures of two or more thereof, in which a mixture of 2-propylheptanol and at least one alcohol selected from the group consisting of 3-methyl-2-propylhexanol, 4-methyl-2-propylhexanol or 5-methyl-2-propylhexanol and the acid(s) desired in the final composition is reacted.

In a preferred embodiment of the invention, the mixture containing alcohol and the acid desired in the final composition is reacted in the presence of an esterification catalyst.

In a preferred embodiment, the mixture containing alcohol and the acid desired in the final composition is heated, the water formed is continuously removed and the crude product is distilled. The process may be carried out in the presence of an esterification catalyst, for example, an acid or a base. In a preferred embodiment, the process is carried out in the absence of solvents, preferably with educts which are substantially water-free. A preferred embodiment of the process is characterized by the use of a tin catalyst. Suitable tin catalysts are, for example, tin oxalate (for example, Fascat® 2001), tin oxide (SnO, Fascat® 2000) and tin(IV) catalysts, such as dibutyl tin diacetate (Fascat® 4200), dibutyl tin oxide (Fascat® 4201) and dibutyl tin laurate (Fascat® 4202) or tin oxide (SnO), which are now marketed by Arkema.

The esterification is preferably carried out at temperatures in the range of from 100° to 300° C. and, more particularly, at temperatures in the range of from 200° to 250° C.

In another embodiment, at least one enzyme is used as the catalyst. Suitable enzymes are any enzymes or enzyme mixtures known to the practitioner which are capable of catalyzing the esterification of alcohol and acid, for example lipases, acyl transferases and esterases. The enzyme-catalyzed esterification is typically carried out at temperatures of 20° to 100° C. and preferably at temperatures of 40° to 80° C.

The present invention also relates to a process for the production of 2-propylheptyl-n-butanoic acid ester, 2-propylheptyl-i-butanoic acid ester, 2-propylheptyl-n-pentanoic acid ester, 2-propylheptyl-i-pentanoic acid ester, 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n-undecenoic acid ester, 2-propylheptyl-i-undecenoic acid ester, 2-propylheptyl-n-dodecanoic acid ester, or 2-propylheptyl-i-dodecanoic acid ester, in which a mixture containing 2-propylheptanol and the methyl ester of the corresponding acid (i.e., n-butanoic acid methyl ester, i-butanoic acid methyl ester, n-pentanoic acid methyl ester, i-pentanoic acid methyl ester, n-hexanoic acid methyl ester, i-hexanoic acid methyl ester, n-heptanoic acid methyl ester, i-heptanoic acid methyl ester, n-octanoic acid methyl ester, i-octanoic acid methyl ester, n-nonanoic acid methyl ester, i-nonanoic acid methyl ester, n-decanoic acid methyl ester, i-decanoic acid methyl ester, n-undecanoic acid methyl ester, i-undecanoic acid methyl ester, n-undecenoic acid methyl ester, i-undecenoic acid methyl ester, n-dodecanoic acid methyl ester or i-dodecanoic acid methyl ester) is reacted in the presence of a transesterification catalyst.

The process according to the invention also encompasses the production of ester mixtures, in which 2-propylheptanol is reacted together with the corresponding mixtures of the methyl esters of the acids in the presence of an esterification catalyst.

The process according to the invention also encompasses the production of the compositions comprising 2-propylheptyl-n-butanoic acid ester and at least one member selected from the group consisting of 3-methyl-2-propylhexyl-n-butanoic acid ester, 4-methyl-2-propylhexyl-n-butanoic acid ester, 5-methyl-2-propylhexyl-n-butanoic acid ester and mixtures of two or more thereof; compositions comprising 2-propylheptyl-i-butanoic acid ester and at least one member selected from the group consisting of 3-methyl-2-propylhexyl-i-butanoic acid ester, 4-methyl-2-propylhexyl-i-butanoic acid ester, 5-methyl-2-propylhexyl-i-butanoic acid ester and mixtures of two or more thereof; compositions containing 2-propylheptyl-n-pentanoic acid ester and at least one member selected from the group consisting of 3-methyl-2-propylhexyl-n-pentanoic acid ester, 4-methyl-2-propylhexyl-n-pentanoic acid ester, 5-methyl-2-propylhexyl-n-pentanoic acid ester and mixtures of two or more thereof; compositions comprising 2-propylheptyl-i-pentanoic acid ester and at least one member selected from the group consisting of 3-methyl-2-propylhexyl-i-pentanoic acid ester, 4-methyl-2-propylhexyl-i-pentanoic acid ester, 5-methyl-2-propylhexyl-i-pentanoic acid ester and mixtures of two or more thereof; compositions comprising 2-propylheptyl-n-hexanoic acid ester and at least one member selected from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof; compositions comprising 2-propylheptyl-i-hexanoic acid ester and at least one member selected from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof; compositions comprising 2-propylheptyl-n-heptanoic acid ester and at least one member selected from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof; compositions comprising 2-propylheptyl-i-heptanoic acid ester and at least one member selected from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures of two or more thereof; compositions comprising 2-propylheptyl-n-octanoic acid ester and at least one member selected from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof; compositions comprising 2-propylheptyl-i-octanoic acid ester and at least one member selected from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof; compositions comprising 2-propylheptyl-n-nonanoic acid ester and at least one member selected from the group consisting of 3-methyl-2-propylhexyl-n-nonanoic acid ester, 4-methyl-2-propylhexyl-n-nonanoic acid ester, 5-methyl-2-propylhexyl-n-nonanoic acid ester and mixtures of two or more thereof; compositions comprising 2-propylheptyl-i-nonanoic acid ester and at least one member selected from the group consisting of 3-methyl-2-propylhexyl-i-nonanoic acid ester, 4-methyl-2-propylhexyl-i-nonanoic acid ester, 5-methyl-2-propylhexyl-i-nonanoic acid ester and mixtures of two or more thereof; compositions comprising 2-propylheptyl-n-decanoic acid ester and at least one member selected from the group consisting of 3-methyl-2-propylhexyl-n-decanoic acid ester, 4-methyl-2-propylhexyl-n-decanoic acid ester, 5-methyl-2-propylhexyl-n-decanoic acid ester and mixtures of two or more thereof; compositions comprising 2-propylheptyl-i-decanoic acid ester and at least one member selected from the group consisting of 3-methyl-2-propylhexyl-i-decanoic acid ester, 4-methyl-2-propylhexyl-i-decanoic acid ester, 5-methyl-2-propylhexyl-i-decanoic acid ester and mixtures of two or more thereof; compositions comprising 2-propylheptyl-n-undecanoic acid ester and at least one member selected from the group consisting of 3-methyl-2-propylhexyl-n-undecanoic acid ester, 4-methyl-2-propylhexyl-n-undecanoic acid ester, 5-methyl-2-propylhexyl-n-undecanoic acid ester and mixtures of two or more thereof; compositions comprising 2-propylheptyl-i-undecanoic acid ester and at least one member selected from the group consisting of 3-methyl-2-propylhexyl-i-undecanoic acid ester, 4-methyl-2-propylhexyl-i-undecanoic acid ester, 5-methyl-2-propylhexyl-i-undecanoic acid ester and mixtures of two or more thereof; compositions comprising 2-propylheptyl-n-undecenoic acid ester and at least one member selected from the group consisting of 3-methyl-2-propylhexyl-n-undecenoic acid ester, 4-methyl-2-propylhexyl-n-undecenoic acid ester, 5-methyl-2-propylhexyl-n-undecenoic acid ester, and mixtures of two or more thereof; compositions comprising 2-propylheptyl-i-undecenoic acid ester and at least one member selected from the group consisting of 3-methyl-2-propylhexyl-i-undecenoic acid ester, 4-methyl-2-propylhexyl-i-undecenoic acid ester, 5-methyl-2-propylhexyl-i-undecenoic acid ester, and mixtures of two or more thereof; compositions comprising 2-propylheptyl-n-dodecanoic acid ester and at least one member selected from the group consisting of 3-methyl-2-propylhexyl-n-dodecanoic acid ester, 4-methyl-2-propylhexyl-n-dodecanoic acid ester, 5-methyl-2-propylhexyl-n-dodecanoic acid ester and mixtures of two or more thereof; and compositions comprising 2-propylheptyl-i-dodecanoic acid ester and at least one member selected from the group consisting of 3-methyl-2-propylhexyl-i-dodecanoic acid ester, 4-methyl-2-propylhexyl-i-dodecanoic acid ester, 5-methyl-2-propylhexyl-i-dodecanoic acid ester and mixtures of two or more thereof, in which a mixture of 2-propylheptanol and at least one alcohol selected from the group consisting of 3-methyl-2-propylhexanol, 4-methyl-2-propylhexanol and 5-methyl-2-propylhexanol, and the methyl ester of the acid desired in the molecules of the final composition is reacted in the presence of a transesterification catalyst.

In a preferred embodiment, the mixture containing alcohol and the methyl ester of the acid desired in the molecules of the final composition is heated in the presence of the esterification catalyst, the water formed is continuously removed and the crude product is distilled. In a preferred embodiment, the process is carried out in the absence of solvents, preferably with educts which are substantially water-free.

The esterification is preferably carried out at temperatures of 100° to 300° C. and more particularly at temperatures of 200° to 250° C. The transesterification catalyst may be selected from any of the transesterification catalysts known to the practitioner, sodium methylate or tetra-alkyl titanate preferably being used.

In another embodiment, at least one enzyme is used as the catalyst. Suitable enzymes are any enzymes or enzyme mixtures known to the practitioner which are capable of catalyzing the transesterification of alcohol and acid methyl ester, for example lipases, acyl transferases and esterases. The enzyme-catalyzed esterification is typically carried out at temperatures of 20° to 100° C., and preferably at temperatures of 40° to 80° C.

Esters of 3-methyl-2-propylhexanol with $C_5$ to $C_{36}$ Carboxylic Acids

The present invention also relates to esters of 3-methyl-2-propylhexanol with linear or branched, saturated or unsaturated $C_5$ to $C_{36}$ carboxylic acids, particularly with $C_5$ to $C_{18}$ carboxylic acids, more particularly with $C_6$ to $C_{12}$ carboxylic acids. Esters of 3-methyl-2-propylhexanol with linear, saturated carboxylic acids are particularly preferred.

More particularly, the present invention relates to 3-methyl-2-propylhexyl-n-butanoic acid ester, 3-methyl-2-propylhexyl-i-butanoic acid ester, 3-methyl-2-propylhexyl-n-pentanoic acid ester, 3-methyl-2-propylhexyl-i-pentanoic acid ester, 3-methyl-2-propylhexyl-n-hexanoic acid ester, 3-methyl-2-propylhexyl-i-hexanoic acid ester, 3-methyl-2-propylhexyl-n-heptanoic acid ester, 3-methyl-2-propylhexyl-i-heptanoic acid ester, 3-methyl-2-propylhexyl-n-octanoic acid ester, 3-methyl-2-propylhexyl-i-octanoic acid ester, 3-methyl-2-propylhexyl-n-nonanoic acid ester, 3-methyl-2-propylhexyl-i-nonanoic acid ester, 3-methyl-2-propylhexyl-n-decanoic acid ester, 3-methyl-2-propylhexyl-i-decanoic acid ester, 3-methyl-2-propylhexyl-n-undecanoic acid ester, 3-methyl-2-propylhexyl-i-undecanoic acid ester, 3-methyl-2-propylhexyl-n-undecenoic acid ester, 3-methyl-2-propylhexyl-i-undecenoic acid ester, 3-methyl-2-propylhexyl-n-dodecanoic acid ester, and 3-methyl-2-propylhexyl-i-dodecanoic acid ester.

The present invention also relates to the use of esters of 3-methyl-2-propylhexanol with linear or branched, saturated or unsaturated carboxylic acids containing 5 to 36 carbon atoms, particularly 5 to 18 carbon atoms, more particularly 6 to 12 carbon atoms, in cosmetic and/or pharmaceutical preparations. Esters of 3-methyl-2-propylhexanol with linear, saturated carboxylic acids are particularly preferred.

The expressions "esters of X-methyl-2-propylhexanol with dicarboxylic acids" used in the following encompass both diesters of the dicarboxylic acids with the particular methyl-2-propylhexanol, i.e. for example, di-3-methyl-2-propylhexyl-n-octanedioic acid diester or di-5-methyl-2-propylhexyl-n-octanedioic acid diester, and also monoesters, such as for example, 3-methyl-2-propylheptyl-n-octanedioic acid monoester, and mixed esters in which one acid group of the dicarboxylic acid is esterified with the particular methyl-2-propylhexanol (the "first methyl-2-propylhexanol") and the second acid group of the dicarboxylic acid is esterified with a second alcohol. The second alcohol may be selected from 3-methyl-2-propylhexanol, 4-methyl-2-propylhexanol and 5-methyl-2-propylhexanol, the second alcohol having to be different from the first methyl-2-propylhexanol.

Another embodiment is characterized by the use of mixed esters of dicarboxylic acids and the particular methyl-2-propylhexanol and another alcohol with the general formula R—OH, where R is a saturated or unsaturated, linear or branched alkyl group containing 1 to 12 carbon atoms.

Another embodiment is characterized by the use of mixed esters of dicarboxylic acids and the particular methyl-2-propylhexanol and another alcohol with the general formula R—OH, where R is a saturated, linear or branched alkyl group containing 1 to 12 carbon atoms.

In another embodiment of the mixed esters, the second alcohol is selected from the group consisting of methanol, ethanol, propanol, isopropanol, butanol, isobutanol, pentanol, hexanol, isohexanol, octanol, decanol and dodecanol.

In a preferred embodiment of the invention, diesters and mixed esters are used as the esters of methyl-2-propylhexanols with $C_4$ to $C_{36}$ dicarboxylic acids.

Esters of 3-methyl-2-propylhexanol with $C_4$ to $C_{36}$ Dicarboxylic Acids

The present invention also relates to esters of 3-methyl-2-propylhexanol with linear or branched, saturated or unsaturated dicarboxylic acids containing 4 to 36 carbon atoms, particularly 4 to 18 carbon atoms, more particularly 6 to 12 carbon atoms. Esters of 3-methyl-2-propylhexanol with linear, saturated dicarboxylic acids are particularly preferred. Diesters of 3-methyl-2-propylhexanol with linear or branched, saturated or unsaturated dicarboxylic acids containing 4 to 36 carbon atoms are also particularly preferred.

More particularly, the present invention relates to di-3-methyl-2-propylhexyl-n-butanedioic acid diester, di-3-methyl-2-propylhexyl-i-butanedioic acid diester, di-3-methyl-2- propylhexyl-n-pentanedioic acid diester, di-3-methyl-2-propylhexyl-i-pentanedioic acid diester, di-3-methyl-2-propylhexyl-n-hexanedioic acid diester, di-3-methyl-2-propylhexyl-i-hexanedioic acid diester, di-3-methyl-2-propylhexyl-n-heptanedioic acid diester, di-3-methyl-2-propylhexyl-i-heptanedioic acid diester, di-3-methyl-2-propylhexyl-n-octanedioic acid diester, di-3-methyl-2-propylhexyl-i-octanedioic acid diester, di-3-methyl-2-propylhexyl-n-nonanedioic acid diester, di-3-methyl-2-propylhexyl-i-nonanedioic acid diester, di-3-methyl-2-propylhexyl-n-decanedioic acid diester, di-3-methyl-2-propylhexyl-i-decanedioic acid diester, di-3-methyl-2-propylhexyl-n-undecanedioic acid diester, di-3-methyl-2-propylhexyl-i-undecanedioic acid diester, di-3-methyl-2-propylhexyl-n-undecenedioic acid diester, di-3-methyl-2-propylhexyl-i-undecenedioic acid diester, di-3-methyl-2-propylhexyl-n-dodecanedioic acid diester, and di-3-methyl-2-propylhexyl-i-dodecanedioic acid diester.

The present invention also relates to the use of esters of 3-methyl-2-propylhexanol with linear or branched, saturated or unsaturated dicarboxylic acids containing 4 to 36 carbon atoms, particularly 4 to 18 carbon atoms, more particularly 6 to 12 carbon atoms in cosmetic and/or pharmaceutical preparations. Esters of 3-methyl-2-propylhexanol with linear, saturated dicarboxylic acids are particularly preferred. Diesters of 3-methyl-2-propylhexanol with linear or branched, saturated or unsaturated dicarboxylic acids containing 4 to 36 carbon atoms are also particularly preferred.

Esters of 4-methyl-2-propylhexanol with $C_5$ to $C_{36}$ Carboxylic Acids

The present invention also relates to esters of 4-methyl-2-propylhexanol with linear or branched, saturated or unsaturated $C_5$ to $C_{36}$ carboxylic acids, particularly with $C_5$ to $C_{18}$ carboxylic acids, more particularly with $C_6$ to $C_{12}$ carboxylic acids. Esters of 4-methyl-2-propylhexanol with linear, saturated carboxylic acids are particularly preferred.

More particularly, the present invention relates to 4-methyl-2-propylhexyl-n-butanoic acid ester, 4-methyl-2-propylhexyl-i-butanoic acid ester, 4-methyl-2-propylhexyl-n-pentanoic acid ester, 4-methyl-2-propylhexyl-i-pentanoic acid ester, 4-methyl-2-propylhexyl-n-hexanoic acid ester, 4-methyl-2-propylhexyl-i-hexanoic acid ester, 4-methyl-2-propylhexyl-n-heptanoic acid ester, 4-methyl-2-propylhexyl-i-heptanoic acid ester, 4-methyl-2-propylhexyl-n-octanoic acid ester, 4-methyl-2-propylhexyl-i-octanoic acid ester, 4-methyl-2-propylhexyl-n-nonanoic acid ester, 4-methyl-2-propylhexyl-i-nonanoic acid ester, 4-methyl-2-propylhexyl-n-decanoic acid ester, 4-methyl-2-propylhexyl-i-decanoic acid ester, 4-methyl-2-propylhexyl-n-undecanoic acid ester, 4-methyl-2-propylhexyl-i-undecanoic acid ester, 4-methyl-2-propylhexyl-n-undecenoic acid ester, 4-methyl-2-propylhexyl-i-undecenoic acid ester, 4-methyl-2-propylhexyl-n-dodecanoic acid ester, and 4-methyl-2-propylhexyl-i-dodecanoic acid ester.

The present invention also relates to the use of esters of 4-methyl-2-propylhexanol with linear or branched, saturated or unsaturated carboxylic acids containing 5 to 36 carbon atoms, particularly 5 to 18 carbon atoms, more particularly 6 to 12 carbon atoms, in cosmetic and/or pharmaceutical preparations. Esters of 4-methyl-2-propylhexanol with linear, saturated carboxylic acids are particularly preferred.

Esters of 4-methyl-2-propylhexanol with $C_4$ to $C_{36}$ Dicarboxylic Acids

The present invention also relates to esters of 4-methyl-2-propylhexanol with linear or branched, saturated or unsaturated dicarboxylic acids containing 4 to 36 carbon atoms, particularly 4 to 18 carbon atoms, more particularly 6 to 12 carbon atoms. Esters of 4-methyl-2-propylhexanol with linear, saturated dicarboxylic acids are particularly preferred. Diesters of 4-methyl-2-propylhexanol with linear or branched, saturated or unsaturated dicarboxylic acids containing 4 to 36 carbon atoms are more particularly preferred.

More particularly, the present invention relates to di-4-methyl-2-propylhexyl-n-butanedioic acid diester, di-4-methyl-2-propylhexyl-i-butanedioic acid diester, di-4-methyl-2-propylhexyl-n-pentanedioic acid diester, di-4-methyl-2-propylhexyl-i-pentanedioic acid diester, di-4-methyl-2-propylhexyl-n-hexanedioic acid diester, di-4-methyl-2-propylhexyl-i-hexanedioic acid diester, di-4-methyl-2-propylhexyl-n-heptanedioic acid diester, di-4-methyl-2-propylhexyl-i-heptanedioic acid diester, di-4-methyl-2-propylhexyl-n-octanedioic acid diester, di-4-methyl-2-propylhexyl-i-octanedioic acid diester, di-4-methyl-2-propylhexyl-n-nonanedioic acid diester, di-4-methyl-2-propylhexyl-i-nonanedioic acid diester, di-4-methyl-2-propylhexyl-n-decanedioic acid diester, di-4-methyl-2-propylhexyl-i-decanedioic acid diester, di-4-methyl-2-propylhexyl-n-undecanedioic acid diester, di-4-methyl-2-propylhexyl-i-undecanedioic acid diester, di-4-methyl-2-propylhexyl-n-undecenedioic acid diester, di-4-methyl-2-propylhexyl-i-undecenedioic acid diester, di-4-methyl-2-propylhexyl-n-dodecanedioic acid diester, and di-4-methyl-2-propylhexyl-i-dodecanedioic acid diester.

The present invention also relates to the use of esters of 4-methyl-2-propylhexanol with linear or branched, saturated or unsaturated dicarboxylic acids containing 4 to 36 carbon atoms, particularly 4 to 18 carbon atoms, more particularly 6 to 12 carbon atoms in cosmetic and/or pharmaceutical preparations. Esters of 4-methyl-2-propylhexanol with linear, saturated dicarboxylic acids are particularly preferred. Diesters of 4-methyl-2-propylhexanol with linear or branched, saturated or unsaturated dicarboxylic acids containing 4 to 36 carbon atoms are also particularly preferred.

Esters of 5-methyl-2-propylhexanol with $C_5$ to $C_{36}$ Carboxylic Acids

The present invention also relates to esters of 5-methyl-2-propylhexanol with linear or branched, saturated or unsaturated carboxylic acids containing 5 to 36 carbon atoms, particularly 5 to 18 carbon atoms, more particularly 6 to 12 carbon atoms. Esters of 5-methyl-2-propylhexanol with linear, saturated carboxylic acids are particularly preferred.

More particularly, the present invention relates to 5-methyl-2-propylhexyl-n-butanoic acid ester, 5-methyl-2-propylhexyl-i-butanoic acid ester, 5-methyl-2-propylhexyl-n-pentanoic acid ester, 5-methyl-2-propylhexyl-i-pentanoic acid ester, 5-methyl-2-propylhexyl-n-hexanoic acid ester, 5-methyl-2-propylhexyl-i-hexanoic acid ester, 5-methyl-2-propylhexyl-n-heptanoic acid ester, 5-methyl-2-propylhexyl-i-heptanoic acid ester, 5-methyl-2-propylhexyl-n-octanoic acid ester, 5-methyl-2-propylhexyl-i-octanoic acid ester, 5-methyl-2-propylhexyl-n-nonanoic acid ester, 5-methyl-2-propylhexyl-i-nonanoic acid ester, 5-methyl-2-propylhexyl-n-decanoic acid ester, 5-methyl-2-propylhexyl-i-decanoic acid ester, 5-methyl-2-propylhexyl-n-undecanoic acid ester, 5-methyl-2-propylhexyl-i-undecanoic acid ester, 5-methyl-2-propylhexyl-n-undecenoic acid ester, 5-methyl-2-propylhexyl-i-undecenoic acid ester, 5-methyl-2-propylhexyl-n-dodecanoic acid ester, and 5-methyl-2-propylhexyl-i-dodecanoic acid ester.

The present invention also relates to the use of esters of 5-methyl-2-propylhexanol with linear or branched, saturated or unsaturated carboxylic acids containing 5 to 36 carbon atoms, particularly 5 to 18 carbon atoms, more particularly 6 to 12 carbon atoms, in cosmetic and/or pharmaceutical preparations. Esters of 5-methyl-2-propylhexanol with linear, saturated carboxylic acids are particularly preferred.

Esters of 5-methyl-2-propylhexanol with $C_4$ to $C_{36}$ Dicarboxylic Acids

The present invention also relates to esters of 5-methyl-2-propylhexanol with linear or branched, saturated or unsaturated dicarboxylic acids containing 4 to 36 carbon atoms, particularly 4 to 18 carbon atoms, more particularly 6 to 12 carbon atoms. Esters of 5-methyl-2-propylhexanol with linear, saturated dicarboxylic acids are particularly preferred. Diesters of 4-methyl-2-propylhexanol with linear or branched, saturated or unsaturated dicarboxylic acids containing 4 to 36 carbon atoms are particularly preferred.

More particularly, the present invention relates to di-5-methyl-2-propylhexyl-n-butanedioic acid diester, di-5-methyl-2-propylhexyl-i-butanedioic acid diester, di-5-methyl-2-propylhexyl-n-pentanedioic acid diester, di-5-methyl-2-propylhexyl-i-pentanedioic acid diester, di-5-methyl-2-propylhexyl-n-hexanedioic acid diester, di-5-methyl-2-propylhexyl-i-hexanedioic acid diester, di-5-methyl-2-propylhexyl-n-heptanedioic acid diester, di-5-methyl-2-propylhexyl-i-heptanedioic acid diester, di-5-methyl-2-propylhexyl-n-octanedioic acid diester, di-5-methyl-2-propylhexyl-i-octanedioic acid diester, di-5-methyl-2-propylhexyl-n-nonanedioic acid diester, di-5-methyl-2-propylhexyl-i-nonanedioic acid diester, di-5-methyl-2-propylhexyl-n-decanedioic acid diester, di-5-methyl-2-propylhexyl-i-decanedioic acid diester, di-5-methyl-2-propylhexyl-n-undecanedioic acid diester, di-5-methyl-2-propylhexyl-i-undecanedioic acid diester, di-5-methyl-2-propylhexyl-n-undecenedioic acid diester, di-5-methyl-2-propylhexyl-i-undecenedioic acid diester, di-5-methyl-2-propylhexyl-n-dodecanedioic acid diester, and di-5-methyl-2-propylhexyl-i-dodecanedioic acid diester.

The present invention also relates to the use of esters of 5-methyl-2-propylhexanol with linear or branched, saturated or unsaturated dicarboxylic acids containing 4 to 36 carbon atoms, particularly 4 to 18 carbon atoms, more particularly 6 to 12 carbon atoms in cosmetic and/or pharmaceutical preparations. Esters of 5-methyl-2-propylhexanol with linear, saturated dicarboxylic acids are particularly preferred. Diesters of 5-methyl-2-propylhexanol with linear or branched, saturated or unsaturated dicarboxylic acids containing 4 to 36 carbon atoms are also particularly preferred.

The present invention also relates to a process for the production of esters of 3-methyl-2-propylhexanol with linear or branched, saturated or unsaturated carboxylic acids containing 5 to 36 carbon atoms, particularly 5 to 18 carbon atoms, more particularly 6 to 12 carbon atoms and/or dicarboxylic acids containing 4 to 36 carbon atoms, particularly 4 to 18 carbon atoms, more particularly 6 to 12 carbon atoms, in which a mixture containing 3-methyl-2-propylhexanol and the carboxylic acid and/or dicarboxylic acid desired in the final molecule is reacted.

The process according to the invention also encompasses the production of ester mixtures, in which 3-methyl-2-propylhexanol is reacted together with the desired carboxylic and/or dicarboxylic acid mixtures.

The process according to the invention also encompasses the production of mixed esters, in which 3-methyl-2-propylhexanol and another alcohol are reacted together with the dicarboxylic acid desired in the final molecule.

The present invention also relates to a process for the production of esters of 4-methyl-2-propylhexanol with linear or branched, saturated or unsaturated carboxylic acids containing 5 to 36 carbon atoms, particularly 5 to 18 carbon atoms, more particularly 6 to 12 carbon atoms and/or dicarboxylic acids containing 4 to 36 carbon atoms, particularly 4 to 18 carbon atoms, more particularly 6 to 12 carbon atoms, in which a mixture containing 4-methyl-2-propylhexanol and the carboxylic acid and/or dicarboxylic acid desired in the final molecule is reacted.

The process according to the invention also encompasses the production of ester mixtures, in which 4-methyl-2-propylhexanol is reacted together with the desired carboxylic and/or dicarboxylic acid mixtures.

The process according to the invention also encompasses the production of mixed esters, in which 4-methyl-2-propylhexanol and another alcohol are reacted together with the dicarboxylic acid desired in the final molecule.

The present invention also relates to a process for the production of esters of 5-methyl-2-propylhexanol with linear or branched, saturated or unsaturated carboxylic acids containing 5 to 36 carbon atoms, particularly 5 to 18 carbon atoms, more particularly 6 to 12 carbon atoms, and/or dicarboxylic acids containing 4 to 36 carbon atoms, particularly 4 to 18 carbon atoms, more particularly 6 to 12 carbon atoms, in which a mixture containing 5-methyl-2-propylhexanol and the carboxylic acid and/or dicarboxylic acid desired in the final molecule is reacted.

The process according to the invention also encompasses the production of ester mixtures, in which 5-methyl-2-propylhexanol is reacted together with the desired carboxylic and/or dicarboxylic acid mixtures.

The process according to the invention also encompasses the production of mixed esters, in which 5-methyl-2-propylhexanol and another alcohol are reacted together with the dicarboxylic acid desired in the final molecule.

In a preferred embodiment of the invention, the mixture containing alcohol (5-methyl-2-propylhexanol, 4-methyl-2-propylhexanol and/or 3-methyl-2-propylhexanol or another alcohol, if any) and the desired carboxylic and/or dicarboxylic acid is reacted in the presence of an esterification catalyst.

In a preferred embodiment of the invention, the mixture containing alcohol (5-methyl-2-propylhexanol, 4-methyl-2-propylhexanol and/or 3-methyl-2-propylhexanol or another alcohol, if any) and the acid desired in the final formula is heated, the water formed is continuously removed and the crude product is then distilled. The process may be carried out in the presence of an esterification catalyst, for example, an acid or a base. In a preferred embodiment, the process is carried out in the absence of solvents, preferably with educts which are substantially water-free. A preferred embodiment of the process is characterized by the use of a tin catalyst. Suitable tin catalysts are, for example, tin oxalate (for example, Fascat® 2001), tin oxide (SnO, Fascat® 2000) and tin(IV) catalysts, such as dibutyl tin diacetate (Fascat® 4200), dibutyl tin oxide (Fascat® 4201) and dibutyl tin laurate (Fascat® 4202) or tin oxide (SnO) which are now marketed by Arkema.

The esterification is preferably carried out at temperatures in the range from 100° to 300° C. and, more particularly, at temperatures in the range from 200° to 250° C.

In another embodiment, at least one enzyme is used as the catalyst. Suitable enzymes are any enzymes or enzyme mixtures known to the practitioner which are capable of catalyzing the esterification of alcohol and acid, for example, lipases, acyl transferases and esterases. The enzyme-catalyzed esterification is typically carried out at temperatures of 20° to 100° C. and preferably at temperatures of 40° to 80° C.

The present invention also relates to a process for the production of esters of 3-methyl-2-propylhexanol with linear or branched, saturated or unsaturated carboxylic acids containing 5 to 36 carbon atoms, particularly 5 to 18 carbon atoms, more particularly 6 to 12 carbon atoms, and/or dicarboxylic acids containing 4 to 36 carbon atoms, particularly 4 to 18 carbon atoms, and more particularly 6 to 12 carbon atoms, in which a mixture containing 3-methyl-2-propylhexanol and the methyl ester of the desired carboxylic or dicarboxylic acid is reacted in the presence of a transesterification catalyst.

The process according to the invention also encompasses the production of mixed esters, in which 3-methyl-2-propylhexanol and another alcohol are reacted together with the methyl or dimethyl ester of the dicarboxylic acid desired in the final molecule in the presence of a transesterification catalyst.

The present invention also relates to a process for the production of esters of 4-methyl-2-propylhexanol with linear or branched, saturated or unsaturated carboxylic acids containing 5 to 36 carbon atoms, particularly 5 to 18 carbon atoms, and more particularly 6 to 12 carbon atoms, and/or dicarboxylic acids containing 4 to 36 carbon atoms, particularly 4 to 18 carbon atoms, and more particularly 6 to 12 carbon atoms, in which a mixture containing 4-methyl-2-propylhexanol and the methyl ester of the carboxylic or dicarboxylic acid desired in the final molecule is reacted in the presence of a transesterification catalyst.

The process according to the invention also encompasses the production of mixed esters, in which 4-methyl-2-propylhexanol and another alcohol are reacted together with the methyl or dimethyl ester of the dicarboxylic acid desired in the final molecule in the presence of a transesterification catalyst.

The present invention also relates to a process for the production of esters of 5-methyl-2-propylhexanol with linear or branched, saturated or unsaturated carboxylic acids containing 5 to 36 carbon atoms, particularly 5 to 18 carbon atoms, more particularly 6 to 12 carbon atoms, and/or dicarboxylic acids containing 4 to 36 carbon atoms, particularly 4 to 18 carbon atoms, more particularly 6 to 12 carbon atoms, in which a mixture containing 5-methyl-2-propylhexanol and the methyl ester of the desired carboxylic and/or dicarboxylic acid(s) is reacted in the presence of a transesterification catalyst.

The process according to the invention also encompasses the production of mixed esters, in which 5-methyl-2-propylhexanol and another alcohol are reacted together with the methyl or dimethyl ester of the dicarboxylic acid desired in the final molecule in the presence of a transesterification catalyst.

The process according to the invention also encompasses the production of ester mixtures, in which the alcohol (5-methyl-2-propylhexanol, 4-methyl-2-propylhexanol, and/or 3-methyl-2-propylhexanol) is reacted together with the mixtures of the methyl esters of the desired carboxylic and/or dicarboxylic acid(s) in the presence of a transesterification catalyst.

In a preferred embodiment, the mixture containing alcohol (5-methyl-2-propylhexanol, 4-methyl-2-propylhexanol, and/or 3-methyl-2-propylhexanol) and the methyl ester of the carboxylic or dicarboxylic acid desired in the final molecule is heated in the presence of the esterification catalyst, the water formed is continuously removed and the crude product is distilled. In a preferred embodiment, the process is carried out in the absence of solvents, preferably with educts which are substantially water-free.

The esterification is preferably carried out at temperatures of 100° to 300° C., and more particularly at temperatures of 200° to 250° C. The transesterification catalyst used may be selected from any of those known to the practitioner, sodium methylate or tetra-alkyl titanate being preferred.

In another embodiment, at least one enzyme is used as the catalyst. Suitable enzymes are any enzymes or enzyme mixtures known to the practitioner, which are capable of catalyzing the transesterification of alcohol and acid methyl ester, for example, lipases, acyl transferases and esterases. The enzyme-catalyzed esterification is typically carried out at temperatures of 20° to 100° C., and preferably at temperatures of 40° to 80° C.

Cosmetic/Pharmaceutical Preparations

The 2-propylheptyl esters allow the production of stable cosmetic and topical pharmaceutical emulsions with a particularly light skin feel.

Accordingly, the present invention relates to cosmetic and/or pharmaceutical preparations containing:
(a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
(b) at least one emulsifier and/or surfactant and/or wax component and/or polymer and/or another oil component.

The present invention also relates to cosmetic and/or pharmaceutical preparations containing
(a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
b-1) at least one emulsifier.

The present invention also relates to cosmetic and/or pharmaceutical preparations containing:
(a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
b-2) at least one surfactant.

The present invention also relates to cosmetic and/or pharmaceutical preparations containing.
(a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
b-3) at least one wax component.

The present invention also relates to cosmetic and/or pharmaceutical preparations containing:
(a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
b-4) at least one polymer.

The present invention also relates to cosmetic and/or pharmaceutical preparations containing:
 (a) at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids, and
 b-5) at least one other oil component.

The preparations according to the invention preferably contain 0.1 to 80% by weight, particularly 0.5 to 70% by weight, more particularly 0.75 to 60% by weight, preferably 1 to 50% by weight, and more preferably 1 to 40% by weight of at least one ester of 2-propylheptanol with linear or branched, saturated or unsaturated $C_5$-$C_{36}$ carboxylic acids or $C_4$-$C_{36}$ dicarboxylic acids.

The present invention also relates to cosmetic and/or pharmaceutical preparations containing
 (a) 0.1 to 80% by weight, particularly 0.1 to 70% by weight, more particularly 0.1 to 60% by weight, preferably 0.1 to 50% by weight, more preferably 0.1 to 40% by weight of at least one ester of 2-propylheptanol with linear or branched, saturated or unsaturated $C_5$-$C_{36}$ carboxylic acids or $C_4$-$C_{36}$ dicarboxylic acids, preferably at least one ester of 2-propylheptanol with linear or branched, saturated or unsaturated $C_5$-$C_{18}$ carboxylic acids or $C_4$-$C_{18}$ dicarboxylic acids,
 b) 0.1 to 20% by weight, in the aggregate, of one or more emulsifiers and/or one or more surfactants and/or one or more wax components and/or one or more polymers,
 b-5) 0.1 to 40% by weight, in the aggregate, of one or more other oil components, and
 c) 0 to 98% by weight of water.

The preparations according to the invention contain at least 0.1, particularly at least 0.5, more particularly at least 0.75, preferably at least 1, and more preferably at least 5% by weight of one or more esters (a).

All percentages by weight represent % by weight, based on the cosmetic and/or pharmaceutical preparation.

In a preferred embodiment of the invention, the preparations comprise esters containing a total of 24 or fewer carbon atoms, preferably 22 or fewer carbon atoms.

The preparations according to the invention preferably contain esters of 2-propylheptanol with carboxylic acids selected from linear or branched, saturated or unsaturated $C_5$ to $C_{36}$ carboxylic acids.

The preparations according to the invention preferably contain esters of 2-propylheptanol with $C_5$ to $C_{30}$, particularly $C_6$ to $C_{24}$, more particularly $C_6$ to $C_{22}$, still more particularly to $C_6$ to $C_{18}$, even still more particularly $C_8$ to $C_{18}$, preferably $C_8$ to $C_{16}$, more preferably $C_8$ to $C_{12}$, still more preferably $C_6$ to $C_{10}$ carboxylic acids or $C_4$ to $C_{30}$, particularly $C_6$ to $C_{24}$, more particularly $C_6$ to $C_{22}$, still more particularly to $C_6$ to $C_{18}$, even still more particularly $C_8$ to $C_{18}$, preferably $C_8$ to $C_{16}$, more preferably $C_8$ to $C_{12}$, still more preferably $C_6$ to $C_{10}$ dicarboxylic acids.

According to the invention, esters of 2-propylheptanol with $C_5$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, or $C_{13}$ or $C_{14}$ carboxylic acids or $C_4$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, or $C_{13}$ or $C_{14}$ dicarboxylic acids are suitable for the preparations according to the invention.

In a particularly preferred embodiment of the invention, the preparations according to the invention contain esters of 2-propylheptanol with $C_6$ to $C_{12}$ carboxylic acids and/or esters of 2-propylheptanol with $C_6$ to $C_{12}$ dicarboxylic acids.

Preferred preparations according to the invention contain esters of 2-propylheptanol with $C_6$ to $C_{16}$ and preferably $C_6$ to $C_{12}$ carboxylic acids or dicarboxylic acids. Of these, linear, unbranched carboxylic acids are preferred. Cosmetic compositions containing 2-propylheptyl caprylate, 2-propylheptyl caproate and/or 2-propylheptyl caprate are particularly preferred.

The preparations according to the invention preferably contain esters of 2-propylheptanol with saturated carboxylic acids and/or esters of 2-propylheptanol with saturated dicarboxylic acids.

According to the invention, the use of esters of 2-propylheptanol with linear, unbranched carboxylic acids and/or esters of 2-propylheptanol with linear, unbranched dicarboxylic acids is preferred in cosmetic and/or topical pharmaceutical preparations.

The preparations according to the invention may contain both individual esters and mixtures of different esters.

In a preferred embodiment of the invention, the preparations contain at least one ester from the group consisting of 2-propylheptyl-n-butanoic acid ester, 2-propylheptyl-i-butanoic acid ester, 2-propylheptyl-n-pentanoic acid ester, 2-propylheptyl-i-pentanoic acid ester, 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n-undecenoic acid ester, 2-propylheptyl-i-undecenoic acid ester, 2-propylheptyl-n-dodecanoic acid ester, and 2-propylheptyl-i-dodecanoic acid ester.

In another embodiment of the invention, the preparations contain at least one composition selected from the group consisting of compositions comprising 2-propylheptyl-n-butanoic acid ester and at least one member selected from the group consisting of 3-methyl-2-propylhexyl-n-butanoic acid ester, 4-methyl-2-propylhexyl-n-butanoic acid ester, 5-methyl-2-propylhexyl-n-butanoic acid ester and mixtures of two or more thereof; compositions comprising 2-propylheptyl-i-butanoic acid ester and at least one member selected from the group consisting of 3-methyl-2-propylhexyl-i-butanoic acid ester, 4-methyl-2-propylhexyl-i-butanoic acid ester, 5-methyl-2-propylhexyl-i-butanoic acid ester and mixtures of two or more thereof; compositions containing 2-propylheptyl-n-pentanoic acid ester and at least one member selected from the group consisting of 3-methyl-2-propylhexyl-n-pentanoic acid ester, 4-methyl-2-propylhexyl-n-pentanoic acid ester, 5-methyl-2-propylhexyl-n-pentanoic acid ester and mixtures of two or more thereof; compositions comprising 2-propylheptyl-i-pentanoic acid ester and at least one member selected from the group consisting of 3-methyl-2-propylhexyl-i-pentanoic acid ester, 4-methyl-2-propylhexyl-i-pentanoic acid ester, 5-methyl-2-propylhexyl-i-pentanoic acid ester and mixtures of two or more thereof; compositions comprising 2-propylheptyl-n-hexanoic acid ester and at least one member selected from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof; compositions comprising 2-propylheptyl-i-hexanoic acid ester and at least one member selected from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof; compositions comprising 2-propylheptyl-n-heptanoic acid ester and at least one member selected from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof; compositions comprising 2-propylheptyl-i-heptanoic acid ester and at least one member selected from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures of two or more thereof; compositions comprising 2-propylheptyl-n-octanoic acid ester and at least one member selected from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof; compositions comprising 2-propylheptyl-i-octanoic acid ester and at least one member selected from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof; compositions comprising 2-propylheptyl-n-nonanoic acid ester and at least one member selected from the group consisting of 3-methyl-2-propylhexyl-n-nonanoic acid ester, 4-methyl-2-propylhexyl-n-nonanoic acid ester, 5-methyl-2-propylhexyl-n-nonanoic acid ester and mixtures of two or more thereof; compositions comprising 2-propylheptyl-i-nonanoic acid ester and at least one member selected from the group consisting of 3-methyl-2-propylhexyl-i-nonanoic acid ester, 4-methyl-2-propylhexyl-i-nonanoic acid ester, 5-methyl-2-propylhexyl-i-nonanoic acid ester and mixtures of two or more thereof; compositions comprising 2-propylheptyl-n-decanoic acid ester and at least one member selected from the group consisting of 3-methyl-2-propylhexyl-n-decanoic acid ester, 4-methyl-2-propylhexyl-n-decanoic acid ester, 5-methyl-2-propylhexyl-n-decanoic acid ester and mixtures of two or more thereof; compositions comprising 2-propylheptyl-i-decanoic acid ester and at least one member selected from the group consisting of 3-methyl-2-propylhexyl-i-decanoic acid ester, 4-methyl-2-propylhexyl-i-decanoic acid ester, 5-methyl-2-propylhexyl-i-decanoic acid ester and mixtures of two or more thereof; compositions comprising 2-propylheptyl-n-undecanoic acid ester and at least one member selected from the group consisting of 3-methyl-2-propylhexyl-n-undecanoic acid ester, 4-methyl-2-propylhexyl-n-undecanoic acid ester, 5-methyl-2-propylhexyl-n-undecanoic acid ester and mixtures of two or more thereof; compositions comprising 2-propylheptyl-i-undecanoic acid ester and at least one member selected from the group consisting of 3-methyl-2-propylhexyl-i-undecanoic acid ester, 4-methyl-2-propylhexyl-i-undecanoic acid ester, 5-methyl-2-propylhexyl-i-undecanoic acid ester and mixtures of two or more thereof; compositions comprising 2-propylheptyl-n-undecenoic acid ester and at least one member selected from the group consisting of 3-methyl-2-propylhexyl-n-undecenoic acid ester, 4-methyl-2-propylhexyl-n-undecenoic acid ester, 5-methyl-2-propylhexyl-n-undecenoic acid ester, and mixtures of two or more thereof; compositions comprising 2-propylheptyl-i-undecenoic acid ester and at least one member selected from the group consisting of 3-methyl-2-propylhexyl-i-undecenoic acid ester, 4-methyl-2-propylhexyl-i-undecenoic acid ester, 5-methyl-2-propylhexyl-i-undecenoic acid ester, and mixtures of two or more thereof; compositions comprising 2-propylheptyl-n-dodecanoic acid ester and at least one member selected from the group consisting of 3-methyl-2-propylhexyl-n-dodecanoic acid ester, 4-methyl-2-propylhexyl-n-dodecanoic acid ester, 5-methyl-2-propylhexyl-n-dodecanoic acid ester and mixtures of two or more thereof; and compositions comprising 2-propylheptyl-i-dodecanoic acid ester and at least one member selected from the group consisting of 3-methyl-2-propylhexyl-i-dodecanoic acid ester, 4-methyl-2-propylhexyl-i-dodecanoic acid ester, 5-methyl-2-propylhexyl-i-dodecanoic acid ester and mixtures of two or more thereof.

In a preferred embodiment of the invention, the preparations contain at least one composition selected from the group consisting of compositions comprising 2-propylheptyl-n-hexanoic acid ester and at least one member selected from the group consisting of 3-methyl-2-propylhexyl-n-hexanoic acid ester, 4-methyl-2-propylhexyl-n-hexanoic acid ester, 5-methyl-2-propylhexyl-n-hexanoic acid ester and mixtures of two or more thereof; compositions comprising 2-propylheptyl-i-hexanoic acid ester and at least one member selected from the group consisting of 3-methyl-2-propylhexyl-i-hexanoic acid ester, 4-methyl-2-propylhexyl-i-hexanoic acid ester, 5-methyl-2-propylhexyl-i-hexanoic acid ester and mixtures of two or more thereof; compositions comprising 2-propylheptyl-n-heptanoic acid ester and at least one member selected from the group consisting of 3-methyl-2-propylhexyl-n-heptanoic acid ester, 4-methyl-2-propylhexyl-n-heptanoic acid ester, 5-methyl-2-propylhexyl-n-heptanoic acid ester and mixtures of two or more thereof; compositions comprising 2-propylheptyl-i-heptanoic acid ester and at least one member selected from the group consisting of 3-methyl-2-propylhexyl-i-heptanoic acid ester, 4-methyl-2-propylhexyl-i-heptanoic acid ester, 5-methyl-2-propylhexyl-i-heptanoic acid ester and mixtures thereof; compositions comprising 2-propylheptyl-n-octanoic acid ester and at least one member selected from the group consisting of 3-methyl-2-propylhexyl-n-octanoic acid ester, 4-methyl-2-propylhexyl-n-octanoic acid ester, 5-methyl-2-propylhexyl-n-octanoic acid ester and mixtures of two or more thereof; and compositions comprising 2-propylheptyl-i-octanoic acid ester and at least one member selected from the group consisting of 3-methyl-2-propylhexyl-i-octanoic acid ester, 4-methyl-2-propylhexyl-i-octanoic acid ester, 5-methyl-2-propylhexyl-i-octanoic acid ester and mixtures of two or more thereof.

In another embodiment of the invention, the preparations contain at least one ester selected from the group consisting of 2-propylheptyl-n-hexanoic acid ester, 2-propylheptyl-n-heptanoic acid ester, 2-propylheptyl-n-octanoic acid ester, 2-propylheptyl-n-nonanoic acid ester, 2-propylheptyl-n-decanoic acid ester, 2-propylheptyl-n-undecanoic acid ester, 2-propylheptyl-n-dodecanoic acid ester and mixtures of two or more thereof.

In a preferred embodiment of the invention, the preparations contain at least one ester selected from the group consisting of 2-propylheptyl-n-hexanoic acid ester, 2-propylheptyl-n-octanoic acid ester, 2-propylheptyl-n-dodecanoic acid ester, 2-propylheptyl-n-dodecanoic acid ester and mixtures of two or more thereof.

In still another embodiment of the invention, the preparations contain at least one ester selected from the group consisting of 2-propylheptyl-n-hexanoic acid ester, 2-propylheptyl-i-hexanoic acid ester, 2-propylheptyl-n-heptanoic acid ester, 2-propylheptyl-i-heptanoic acid ester, 2-propylheptyl-n-octanoic acid ester, 2-propylheptyl-i-octanoic acid ester, 2-propylheptyl-n-nonanoic acid ester, 2-propylheptyl-i-nonanoic acid ester, 2-propylheptyl-n-decanoic acid ester, 2-propylheptyl-i-decanoic acid ester, 2-propylheptyl-n-undecanoic acid ester, 2-propylheptyl-i-undecanoic acid ester, 2-propylheptyl-n-dodecanoic acid ester, and 2-propylheptyl-i-dodecanoic acid ester.

In a preferred embodiment of the invention, the preparations contain at least one ester selected from the group consisting of 2-propylheptyl-n-hexanoic acid ester, 2-propylheptyl-i-hexanoic acid ester, 2-propylheptyl-n-n-octanoic acid ester, 2-propylheptyl-i-octanoic acid ester, 2-propylheptyl-n-decanoic acid ester, 2-propylheptyl-i-decanoic acid ester, 2-propylheptyl-n-dodecanoic acid ester, 2-propylheptyl-i-dodecanoic acid ester and mixtures of two or more thereof.

Another preferred embodiment of the cosmetic and/or pharmaceutical preparations contains (a) 0.1 to 80, particularly 0.1 to 70, preferably 0.1 to 60, and more preferably 0.1 to 50% by weight of at least one ester of 2-propylheptanol with linear or branched, saturated or unsaturated $C_5$-$C_{36}$ carboxylic acids or $C_4$-$C_{36}$ dicarboxylic acids, (b) 0.1 to 20% by weight, in the aggregate, of one or more emulsifiers and/or one or more surfactants and/or one or more wax components and/or one or more polymers and 0.1 to 40% by weight, in the aggregate, of one or more other oil components and (d) 0 to 98% by weight of water.

The expression "esters of 2-propylheptanol with dicarboxylic acids" encompasses both diesters of dicarboxylic acids with 2-propylheptanol, i.e., for example, di-2-propylheptyl-n-octanedioic acid diester, and monoesters, such as 2-propylheptyl-n-octanedioic acid monoester, for example, and mixed esters, in which one acid group of the dicarboxylic acid is esterified with 2-propylheptanol and the second acid group of the dicarboxylic acid is esterified with another alcohol. Another embodiment of the invention is characterized by the use of mixed esters of dicarboxylic acids and 2-propylheptanol and another alcohol selected from the group consisting of 3-methyl-2-propylhexanol, 4-methyl-2-propylhexanol and 5-methyl-2-propylhexanol. In a preferred embodiment of the invention, the mixed esters are obtained by reaction of the corresponding dicarboxylic acid with a mixture of 2-propylheptanol, 3-methyl-2-propylhexanol, 4-methyl-2-propylhexanol and 5-methyl-2-propylhexanol.

Another embodiment is characterized by the use of mixed esters of dicarboxylic acids and 2-propylheptanol and another alcohol with the general formula R—OH, where R is a linear or branched, saturated or unsaturated alkyl group containing 1 to 12 carbon atoms.

Still another embodiment is characterized by the use of mixed esters of dicarboxylic acids and 2-propylheptanol and another alcohol with the general formula R—OH, where R is a saturated, linear or branched alkyl group containing 1 to 12 carbon atoms.

A preferred embodiment is characterized by the use of mixed esters of dicarboxylic acids and 2-propylheptanol and another alcohol, the other alcohol being selected from the group consisting of methanol, ethanol, propanol, isopropanol, butanol, isobutanol, pentanol, hexanol, isohexanol, octanol, decanol or dodecanol.

In a preferred embodiment of the invention, diesters and mixed esters are used as the esters of 2-propylheptanol with $C_4$ to $C_{36}$ dicarboxylic acids.

In another preferred embodiment, the preparations according to the invention contain esters of 2-propylheptanol with linear or branched, saturated or unsaturated $C_4$ to $C_{32}$ dicarboxylic acids, particularly $C_4$ to $C_{30}$, more particularly $C_6$ to $C_{24}$, still more particularly $C_6$ to $C_{22}$, most particularly $C_8$ to $C_{18}$, preferably $C_8$ to $C_{16}$, more preferably $C_8$ to $C_{16}$, and still more preferably $C_8$ to $C_{12}$ dicarboxylic acids.

According to the invention, esters of 2-propylheptanol with $C_4$ to $C_{36}$, $C_5$ to $C_{30}$, $C_6$ to $C_{26}$, $C_7$ to $C_{24}$, $C_8$ to $C_{22}$, $C_9$ to $C_{20}$, $C_{10}$ to $C_{18}$, $C_{11}$ to $C_{17}$, $C_{11}$ to $C_{16}$, $C_{12}$ to $C_{15}$, or $C_{13}$ or $C_{14}$ dicarboxylic acids are suitable for the preparations according to the invention.

In a particularly preferred embodiment of the invention, the preparations contain esters of 2-propylheptanol with $C_6$ to $C_{12}$ dicarboxylic acids.

According to the invention, esters of 2-propylheptanol with saturated dicarboxylic acids are preferred, as are esters of 2-propylheptanol with linear, unbranched dicarboxylic acids.

Suitable diesters of the dicarboxylic acids of 2-propylheptanol are di-2-propylheptyl-n-butanedioic acid diester, di-2-propylheptyl-i-butanedioic acid diester, di-2-propylheptyl-n-pentanedioic acid diester, di-2-propylheptyl-i-pentanedioic acid diester, di-2-propylheptyl-n-hexanedioic acid diester, di-2-propylheptyl-i-hexanedioic acid diester, di-2-propylheptyl-n-heptanedioic acid diester, di-2-propylheptyl-i-heptanedioic acid diester, di-2-propylheptyl-n-octanedioic acid diester, di-2-propylheptyl-i-octanedioic acid diester, di-2-propylheptyl-n-nonanedioic acid diester, di-2-propylheptyl-i-nonanedioic acid diester, di-2-propylheptyl-n-decanedioic acid diester, di-2-propylheptyl-i-decanedioic acid diester, di-2-propylheptyl-n-undecanedioic acid diester, di-2-propylheptyl-i-undecanedioic acid diester, di-2-propylheptyl-n-undecenedioic acid diester, di-2-propylheptyl-i-undecenedioic acid diester, di-2-propylheptyl-n-dodecanedioic acid diester, di-2-propylheptyl-i-dodecanedioic acid diester.

Suitable mixed esters of dicarboxylic acids of 2-propylheptanol and methanol are 2-propylheptylmethyl-n-butanedioic acid diester, di-2-propylheptylmethyl-i-butanedioic acid diester, di-2-propylheptylmethyl-n-pentanedioic acid diester, di-2-propylheptylmethyl-i-pentanedioic acid diester, di-2-propylheptylmethyl-n-hexanedioic acid diester, di-2-propylheptylmethyl-i-hexanedioic acid diester, di-2-propylheptylmethyl-n-heptanedioic acid diester, di-2-propylheptylmethyl-i-heptanedioic acid diester, di-2-propylheptylmethyl-n-octanedioic acid diester, di-2-propylheptylmethyl-i-octanedioic acid diester, di-2-propylheptylmethyl-n-nonanedioic acid diester, di-2-propylheptylmethyl-i-nonanedioic acid diester, di-2-propylheptylmethyl-n-decanedioic acid diester, di-2-propylheptylmethyl-i-decanedioic acid diester, di-2-propylheptylmethyl-n-undecanedioic acid diester, di-2-propylheptylmethyl-i-undecanedioic acid diester, di-2-propylheptylmethyl-n-undecenedioic acid diester, di-2-propylheptylmethyl-i-undecenedioic acid diester, di-2-propylheptylmethyl-n-dodecanedioic acid diester, and di-2-propylheptylmethyl-i-dodecanedioic acid diester.

Corresponding mixed esters of dicarboxylic acids of 2-propylheptanol and at least one other alcohol with the general formula R—OH, where R is a linear or branched, saturated or unsaturated alkyl group containing 1 to 12 carbon atoms, are also included.

More particularly, corresponding mixed esters of dicarboxylic acids and 2-propylheptanol and at least one other alcohol are included, the other alcohol being selected from the group consisting of ethanol, propanol, isopropanol, butanol, isobutanol, pentanol, hexanol, isohexanol, octanol, decanol and dodecanol.

The present invention also relates to the use of at least one member selected from di-2-propylheptyl-n-butanedioic acid diester, di-2-propylheptyl-i-butanedioic acid diester, di-2-propylheptyl-n-pentanedioic acid diester, di-2-propylheptyl-i-pentanedioic acid diester, di-2-propylheptyl-n-hexanedioic acid diester, di-2-propylheptyl-i-hexanedioic acid diester, di-2-propylheptyl-n-heptanedioic acid diester, di-2-propylheptyl-i-heptanedioic acid diester, di-2-propylheptyl-n-octanedioic acid diester, di-2-propylheptyl-i-octanedioic acid diester, di-2-propylheptyl-n-nonanedioic acid diester, di-2-propylheptyl-i-nonanedioic acid diester, di-2-propylheptyln-decanedioic acid diester, di-2-propylheptyl-i-decanedioic acid diester, di-2-propylheptyl-n-undecanedioic acid diester, di-2-propylheptyl-i-undecanedioic acid diester, di-2-propylheptyl-n-undecenedioic acid diester, di-2-propylheptyl-i-undecenedioic acid diester, di-2-propylheptyl-n-dodecanedioic acid diester, di-2-propylheptyl-i-dodecanedioic acid diester, 2-propylheptyl-n-butanedioic acid monoester, 2-propylheptyl-i-butanedioic acid monoester, 2-propylheptyl-n-pentanedioic acid monoester, 2-propylheptyl-i-pentanedioic acid monoester, 2-propylheptyl-n-hexanedioic acid monoester, 2-propylheptyl-i-hexanedioic acid monoester, 2-propylheptyl-n-heptanedioic acid monoester, 2-propylheptyl-i-heptanedioic acid monoester, 2-propylheptyl-n-octanedioic acid monoester, 2-propylheptyl-i-octanedioic acid monoester, 2-propylheptyl-n-nonanedioic acid monoester, 2-propylheptyl-i-nonanedioic acid monoester, 2-propylheptyl-n-decanedioic acid monoester, 2-propylheptyl-i-decanedioic acid monoester, 2-propylheptyl-n-undecanedioic acid monoester, 2-propylheptyl-i-undecanedioic acid monoester, 2-propylheptyl-n-undecenedioic acid monoester, 2-propylheptyl-i-undecenedioic acid monoester, 2-propylheptyl-n-dodecanedioic acid monoester, 2-propylheptyl-i-dodecanedioic acid monoester and mixtures of two or more thereof in cosmetic and/or pharmaceutical preparations.

The present invention also relates to compositions containing esters of 2-propylheptanol with $C_4$-$C_{36}$ dicarboxylic acids and at least one member selected from the group consisting of esters of $C_4$-$C_{36}$ dicarboxylic acids with at least one member selected from the group consisting of 3-methyl-2-propylhexanol, 4-methyl-2-propylhexanol and 5-methyl-2-propylhexanol and mixtures of two or more thereof, and to their use in cosmetic and/or pharmaceutical preparations.

Compositions containing esters of 2-propylheptanol with $C_4$-$C_{18}$ dicarboxylic acids, more particularly $C_6$ to $C_{12}$ dicarboxylic acids, and at least one member selected from the group consisting of esters of $C_4$ to $C_{18}$, and more particularly $C_6$ to $C_{12}$ dicarboxylic acids, with at least one member selected from the group consisting of 3-methyl-2-propylhexanol, 4-methyl-2-propylhexanol, 5-methyl-2-propylhexanol and mixtures of two or more thereof are suitable for use in cosmetic and/or pharmaceutical preparations, and are particularly preferred.

The present invention relates to compositions containing esters of 2-propylheptanol with n-butanedioic acids and at least one member selected from the group consisting of esters of n-butanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid, for example, di-2-propylheptyl-n-butanedioic acid diester and di-5-methyl-2-propylhexyl-n-butanedioic acid diester.

The present invention also relates to compositions containing esters of 2-propylheptanol with i-butanedioic acid, and at least one member selected from the group consisting of esters of i-butanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with n-pentanedioic acid, and at least one member selected from the group consisting of esters of n-pentanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-pentanedioic acid and at least one member selected from the group consisting of esters of i-pentanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention further relates to compositions containing esters of 2-propylheptanol with n-hexanedioic acid and at least one member selected from the group consisting of esters of n-hexanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-hexanedioic acid and at least one member selected from the group consisting of esters of i-hexanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention relates to compositions containing esters of 2-propylheptanol with n-heptanedioic acid and at least one member selected from the group consisting of esters of n-heptanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-heptanedioic acid and at least one member selected from the group consisting of esters of i-heptanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention additionally relates to compositions containing esters with 2-propylheptanol of n-octanedioic acid and at least one member selected from the group consisting of esters of n-octanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with i-octanedioic acid and at least one member selected from the group consisting of esters of i-octanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with n-nonanedioic acid and at least one member selected from the group consisting of esters of n-nonanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-nonanedioic acid and at least one member selected from the group consisting of esters of i-nonanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention further relates to compositions containing esters of 2-propylheptanol with n-decanedioic acid and at least one member selected from the group consisting of esters of n-decanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention relates to compositions containing esters of 2-propylheptanol with i-decanedioic acid and at least one member selected from the group consisting of esters of i-decanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-undecanedioic acid and at least one member selected from the group consisting of esters of n-undecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with i-undecanedioic acid and at least one member selected from the group consisting of esters of i-undecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention additionally relates to compositions containing esters of 2-propylheptanol with n-undecenedioic acid and at least one member selected from the group consisting of esters of n-undecenedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-undecenedioic acid and at least one member selected from the group consisting of esters of i-undecenedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-dodecanedioic acid and at least one member selected from the group consisting of esters of n-dodecanedioic acid with at least one member selected from the group consisting of 3-methyl-2-propylhexanol, 4-methyl-2-propylhexanol and 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention relates to compositions containing esters of 2-propylheptanol with i-dodecanedioic acid and at least one member selected from the group consisting of esters of i-dodecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention further relates to compositions containing esters of 2-propylheptanol with n-tridecanedioic acid and at least one member selected from the group consisting of esters of n-tridecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-tridecanedioic acid and at least one member selected from the group consisting of esters of i-tridecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-tetradecanedioic acid and at least one member selected from the group consisting of esters of n-tetradecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-tetradecanedioic acid and at least one member selected from the group consisting of esters of i-tetradecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention additionally relates to compositions containing esters of 2-propylheptanol with n-pentadecanedioic acid and at least one member selected from the group consisting of esters of n-pentadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention relates to compositions containing esters of 2-propylheptanol with i-pentadecanedioic acid and at least one member selected from the group consisting of esters of i-pentadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-hexadecanedioic acid and at least one member selected from the group consisting of esters of n-hexadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-hexadecanedioic acid and at least one member selected from the group consisting of esters of i-hexadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention further relates to compositions containing esters of 2-propylheptanol with n-heptadecanedioic acid and at least one member selected from the group consisting of esters of n-heptadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-heptadecanedioic acid and at least one member selected from the group consisting of esters of i-heptadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with n-octadecanedioic acid and at least one member selected from the group consisting of esters of n-octadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention relates to compositions containing esters of 2-propylheptanol with i-octadecanedioic acid and at least one member selected from the group consisting of esters of i-octadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention additionally relates to compositions containing esters of 2-propylheptanol with n-nonadecanedioic acid and at least one member selected from the group consisting of esters of n-nonadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-nonadecanedioic acid and at least one member selected from the group consisting of esters of i-nonadecanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-eicosanedioic acid and at least one member selected from the group consisting of esters of n-eicosanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acid.

The present invention also relates to compositions containing esters of 2-propylheptanol with i-eicosanedioic acid and at least one member selected from the group consisting of esters of i-eicosanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention additionally relates to compositions containing esters of 2-propylheptanol with n-docosanedioic acid and at least one member selected from the group consisting of esters of n-docosanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention relates to compositions containing esters of 2-propylheptanol with i-docosanedioic acid and at least one member selected from the group consisting of esters of i-docosanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with n-tetracosanedioic acid and at least one member selected from the group consisting of esters of n-tetracosanedioic acid with at least one member selected from the group consisting of 3-methyl-2-propylhexanol, 4-methyl-2-propylhexanol, and 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-tetracosanedioic acid and at least one member selected from the group consisting of esters of i-tetracosanedioic acid with at least one member selected from the group consisting of 3-methyl-2-propylhexanol, 4-methyl-2-propylhexanol, 5-methyl-2-propylhexanol and mixtures of two or more thereof, and to their use in cosmetic and/or pharmaceutical preparations. In another preferred embodiment of the invention, the composition contains the diesters of the dicarboxylic acids.

The present invention also relates to compositions containing esters of 2-propylheptanol with n-hexacosanedioic acid and at least one member selected from the group consisting of esters of n-hexacosanedioic acid with at least one member selected from the group consisting of 3-methyl-2-propylhexanol, 4-methyl-2-propylhexanol, and 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to compositions containing esters of 2-propylheptanol with i-hexacosanedioic acid and at least one member selected from the group consisting of esters of i-hexacosanedioic acid with at least one member selected from the group consisting of 3-methyl-2-propylhexanol, 4-methyl-2-propylhexanol, and 5-methyl-2-propylhexanol and mixtures of two or more thereof, and to their use in cosmetic and/or pharmaceutical preparations. In a preferred embodiment of the invention, the composition contains the diesters of the dicarboxylic acid.

The present invention also relates to esters of 2-propylheptanol with dimer fatty acids (polycarboxylic acids which are obtained by polymerization of unsaturated fatty acids, mainly oleic acid or tall oil fatty acid, with commercial such acids consisting of a mixture which, apart from small amounts of linear and branched $C_{18}$ monocarboxylic acids (monomer fatty acid), mainly contains $C_{36}$ dicarboxylic acid and different levels of $C_{54}$ tricarboxylic acid (trimer fatty acid), with traces of higher polymer fatty acids).

The present invention further relates to compositions containing esters of 2-propylheptanol with dimer fatty acids and at least one member selected from the group consisting of esters of 3-methyl-2-propylhexanol with dimer fatty acids, esters of 4-methyl-2-propylhexanol with dimer fatty acids, esters of 5-methyl-2-propylhexanol with dimer fatty acids and mixtures of two or more thereof, and to their use in cosmetic and/or pharmaceutical preparations. In a preferred embodiment of the invention, the composition contains the diesters of the dimer fatty acids.

The preparations according to the invention, the compositions according to the invention and the esters according to the invention are suitable for incorporation as a base in all cosmetic body care and cleansing preparations, such as, for example, body oil, baby oil, body milk, creams, lotions, sprayable emulsions, sunscreens, antiperspirants, liquid and bar soaps, etc. They may also be used in surfactant-containing formulations, such as, for example, foam and shower baths, hair shampoos and hair care rinses. They may be applied as a care component to tissues, papers, wipes, nonwovens, sponges, puffs, plasters and bandages which are used in the field of hygiene and care (e.g., wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products, and self-tanning wipes). They may also be used in other hair-care, hair-cleaning or hair-coloring preparations.

Depending on the application envisaged, the cosmetic formulations contain a number of auxiliaries, additives and other ingredients, such as, for example, surfactants, other oil components, emulsifiers, pearlizing waxes, consistency factors, thickeners, superfatting agents, stabilizers, polymers, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc., which are listed, by way of example, in the following.

Emulsifier

In one embodiment of the invention, the preparations according to the invention contain at least one emulsifier. The compositions according to the invention contain one or more emulsifiers in a quantity of 0 to 40% by weight, preferably 0.1 to 20% by weight, more preferably 0.1 to 15% by weight, and still more preferably 0.1 to 10% by weight, based on the total weight of the composition.

In one embodiment of the invention, the preparation according to the invention contains more than one emulsifier. Depending on the other components, the practitioner may use typical emulsifier systems (such as, for example, emulsifier and co-emulsifier) with the compositions according to the invention.

Nonionic Emulsifiers

The group of nonionic emulsifiers includes, for example, (1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;

(2) $C_{12-18}$ fatty acid monoesters and diesters of products of the addition of 1 to 50 mol ethylene oxide onto glycerol;

(3) sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) products of the addition of 7 to 60 mol ethylene oxide onto castor oil and/or hydrogenated castor oil;

(6) polyol esters and, in particular, polyglycerol esters, such as, for example, polyolpoly-12-hydroxystearate, polyglycerol polyricinoleate, polyglycerol diisostearate or polyglycerol dimerate, as well as mixtures of compounds from several of these classes;

(7) products of the addition of 2 to 15 mol ethylene oxide onto castor oil and/or hydrogenated castor oil;

(8) partial esters based on linear or branched, unsaturated or saturated $C_{6-22}$ fatty acids, ricinoleic acid and 12-hydroxystearic acid and polyglycerol, pentaerythritol, dipentaerythritol, sugar alcohols (for example, sorbitol), alkyl glucosides (for example, methyl glucoside, butyl glucoside, and lauryl glucoside) and polyglucosides (for example, cellulose) or mixed esters, such as glyceryl stearate citrate and glyceryl stearate lactate, for example;

(9) polysiloxane/polyalkyl polyether copolymer or corresponding derivatives;

(10) mixed esters of pentaerythritol, fatty acids, citric acid and fatty alcohol and/or mixed esters of fatty acids containing 6 to 22 carbon atoms, methyl glucose and polyols, preferably glycerol or polyglycerol.

The addition products of ethylene oxide and/or propylene oxide onto fatty alcohols, fatty acids, alkylphenols, glycerol monoesters and diesters, and sorbitan monoesters and diesters of fatty acids, or onto castor oil are known commercially-available products. They are homolog mixtures of which the average degree of alkoxylation corresponds to the ratio between the quantities of ethylene oxide and/or propylene oxide and substrate with which the addition reaction is carried out. These emulsifiers are water-in-oil (w/o) or oil-in-water (o/w) emulsifiers, depending on the degree of ethoxylation. $C_{12/18}$ fatty acid monoesters and diesters of addition products of ethylene oxide onto glycerol are known as lipid layer enhancers for cosmetic preparations.

According to the invention, particularly suitable and mild emulsifiers are the polyol poly-12-hydroxystearates and mixtures thereof marketed by Cognis Deutschland GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier). Particular reference is made in this connection to EP 0 766 661 B1. The polyol component of these emulsifiers may be derived from substances which contain at least two, preferably 3 to 12, and more particularly 3 to 8 hydroxyl groups, and 2 to 12 carbon atoms.

In principle, suitable lipophilic w/o emulsifiers are emulsifiers with an HLB value of 1 to 8 which are listed in numerous Tables and are well-known to the practitioner. Some of these emulsifiers are listed, for example, in Kirk-Othmer, *Encyclopedia of Chemical Technology*, 3rd Edition, 1979, Vol. 8, page 913. The HLB value for ethoxylated products may also be calculated to the following formula: HLB=(100−L): 5, where L is the percentage by weight of lipophilic groups, i.e., fatty alkyl or fatty acyl groups, in percent by weight in the ethylene oxide adducts.

Of particular advantage from the group of w/o emulsifiers are partial esters of polyols, more particularly $C_{4-6}$ polyols, such as, for example, partial esters of pentaerythritol or sugar esters, for example, sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

Depending on the formulation, it can be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example, 10-20 ethylene oxide units for o/w emulsifiers and 20-40 ethylene oxide units for the solubilizers. Particularly advantageous o/w emulsifiers for the purposes of the invention are Ceteareth-12 and PEG-20 Stearate. Particularly suitable solubilizers are Eumulgin® HRE 40 (INCI name: PEG-40 Hydrogenated Castor oil), Eumulgin® HRE 60 (INCI name: PEG-60 Hydrogenated Castor Oil), Eumulgin® L (INCI name: PPG-1-PEG-9 Laurylglycolether) and Eumulgin® SML 20 (INCI name: Polysorbat-20).

Nonionic emulsifiers from the group of alkyl oligoglycosides are particularly compatible with the skin (e.g., $C_{8-22}$ alkyl mono- and oligoglycosides, their production and their use being known from the prior art). Such oligoglycosides are produced by reacting glucose or oligosaccharides with primary alcohols containing 8 to 22 carbon atoms. So far as the glycoside component is concerned, both monoglycosides, where a cyclic sugar unit is attached to the fatty alcohol by a glycoside bond, and oligomeric glycosides with a degree of oligomerization of preferably up to about 8, are suitable. The degree of oligomerization is a statistical mean value on which a homolog distribution typical of such technical products is based. Products available under the trademark, Plantacare®, contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the trademark, Emulgade® PL 68/50 by Cognis Deutschland GmbH, which is a 1:1 mixture of alkyl polyglucosides and fatty alcohols, is preferred for the purposes of the invention. According to the invention, the mixture of lauryl glucoside, polyglyceryl-2-dipolyhydroxystearate, glycerol and water, which is marketed as Eumulgin® VL 75, may also be used with advantage in accordance with the invention.

Other suitable emulsifiers are such substances as lecithins and phospholipids. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are generally classed as fats. Sphingosines and sphingolipids are also suitable as fat-like substances.

Surfactants

In one embodiment of the invention, the preparations according to the invention contain at least one surfactant. The surfactant(s) may be selected from anionic, nonionic, cationic and/or amphoteric or zwitterionic surfactants. Surfactant-containing cosmetic preparations, such as for example shower gels, foam baths, shampoos, etc., preferably contain at least one anionic surfactant.

The compositions according to the invention contain the surfactant(s), in the aggregate, in a quantity of 0 to 40% by weight, preferably 0 to 20% by weight, more preferably 0.1 to 15% by weight, and still more particularly 0.1 to 10% by weight, based on the total weight of the composition.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_{8-18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12-18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

Wax Component

In one embodiment of the invention, the preparations according to the invention contain at least one wax component. The compositions according to the invention contain the wax component(s) in a quantity of 0 to 40% by weight, particularly 0 to 20% by weight, preferably 0.1 to 15% by weight and more preferably 0.1 to 10% by weight, based on the total weight of the composition.

Waxes are normally understood to be natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A single wax component or a mixture of wax components melting at or above 30° C. may be used in accordance with the invention.

According to the invention, fats and fat-like substances with a wax-like consistency may also be used as waxes providing they have the required melting point. These include, inter alia, fats (triglycerides), mono- and diglycerides, natural and synthetic waxes, fat and wax alcohols, fatty acids, esters of fatty alcohols and fatty acids and fatty acid amides or mixtures of these substances.

Fats in the context of the invention are understood to be triacylglycerols, i.e., the triple esters of fatty acids with glycerol. The triacylglycerols preferably contain saturated, unbranched and unsubstituted fatty acid components. They may also be mixed esters, i.e., triple esters of glycerol with various fatty acids. So-called hardened fats and oils obtained by partial hydrogenation may be used in accordance with the invention and are particularly suitable as consistency factors. Vegetable hardened fats and oils, for example, hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are, inter alia, the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the trademark Cutina® HR. Glycerol tristearate, glycerol tribehenate (for example Syncrowax® HRC), glycerol tripalmitate or the triglyceride mixtures known under the trademark Syncrowax® HGLC are also suitable providing the melting point of the wax component or the mixture is 30° C. or higher.

According to the invention, suitable wax components are, in particular, mono- and diglycerides and mixtures of these partial glycerides. Glyceride mixtures suitable for use in accordance with the invention include the products Novata® AB and Novata® B (mixture of $C_{12-18}$ mono-, di- and triglycerides) and Cutina® MD or Cutina® GMS (glyceryl stearate) marketed by Cognis Deutschland GmbH.

The fatty alcohols suitable for use as a wax component in accordance with the invention include $C_{12-50}$ fatty alcohols. The fatty alcohols may be obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated unbranched fatty alcohols are preferred. However, unsaturated, branched or unbranched fatty alcohols may also be used as the wax component in accordance with the invention providing they have the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols) or the partly branched alcohols from the oxosynthesis (Dobanols) may also be used. $C_{14-22}$ fatty alcohols marketed for example by Cognis Deutschland GmbH under the name of Lanette® 16 ($C_{16}$ alcohol), Lanette® 14 ($C_{14}$ alcohol), Lanette® 0 ($C_{16/18}$ alcohol) and Lanette® 22 ($C_{18/22}$ alcohol) are particularly suitable for the purposes of the invention. Fatty alcohols give the compositions a dryer feeling on the skin than triglycerides.

$C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use in accordance with the invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Examples of esters such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers

In one embodiment of the invention, the preparations according to the invention contain at least one polymer. The compositions according to the invention contain the polymer(s) in a quantity of 0 to 20% by weight, preferably 0.1 to 15% by weight and, more particularly, 0.1 to 10% by weight, based on the total weight of the composition.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat®550, Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Other suitable polymers are polysaccharides, more particularly xanthan gum, guar guar, agar agar, alginates and tyloses.

Other Oil Components

Body-care preparations, such as creams, body oils, lotions and milks, typically contain a number of other oil components and emollients which contribute towards further optimizing the sensory properties. The oil components (esters according to the invention plus other oil components) are typically present in a total quantity of 0.1 to 80, more particularly 0.5 to 70, preferably 1 to 60, more particularly 1 to 50% by weight, more particularly 1 to 40% by weight, preferably 5 to 25% by weight and more particularly 5 to 15% by weight. The other oil components are typically present in a quantity of 0.1 to 40% by weight.

The other oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18-38}$ alkyl-hydroxycarboxylic acids with linear or branched $C_{6-22}$ fatty alcohols, more especially dioctyl malate, esters of linear and/or branched fatty acids with polyhydric alcohols (for example propylene glycol, dimer diol or trimer triol), triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols and hydrocarbons or mixtures thereof (Cetiol® DD).

Other Ingredients

Suitable thickeners are, for example, Aerosil® types (hydrophilic silicas), carboxymethyl cellulose and hydroxyethyl and hydroxypropyl cellulose, polyvinyl alcohol, polyvinyl pyrrolidone and bentonites, for example Bentone® Gel VS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are often combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers.

Suitable insect repellents are N,N-diethyl-m-toluamide, pentane-1,2-diol or 3-(N-n-butyl-N-acetylamino)-propionic acid ethyl ester), which is marketed as Insect Repellent 3535 by Merck KGaA, and Butylacetylaminopropionate.

A suitable self-tanning agent is, for example, dihydroxyacetone. Suitable tyrosine inhibitors, which prevent the formation of melanin and are used in depigmenting agents, are, for example, arbutin, ferulic acid, koji acid, coumaric acid and ascorbic acid (vitamin C).

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are mixtures of natural and synthetic perfumes. Natural perfumes are extracts of flowers, stems and leaves, fruits, fruit peel, roots, woods, herbs and grasses, needles and branches, resins and balsams. Also suitable are animal raw materials, for example civet and beaver, and synthetic perfume compounds of the ester, ether, aldehyde, ketone, alcohol and hydrocarbon type.

Suitable pearlizing waxes, particularly for use in surfactant-containing formulations, are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Superfatting agents may be selected from such substances as, for example, lanolin and lecithin and also polyethoxylated or acylated lanolin and—lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen.

The preparations according to the invention, the compositions according to the invention and the esters according to the invention are suitable, particularly in cosmetic and/or pharmaceutical preparations, for wetting or impregnating or coating utility and hygiene wipes which are used for care and/or cleansing of the body.

Examples of utility and hygiene wipes include tissues, papers, wipes, nonwovens, sponges, puffs, plasters and bandages which are used in the field of hygiene and care. These may be wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products and self-tanning wipes.

EXAMPLES

Example 1a

Production of 2-propylheptyl Caprylate by Esterification 158.3 g 2-propylheptanol (1 mol) and 144.2 g caprylic acid (1 mol) were heated for 5 h to 220° C. on a water separator together with 0.30 g Fascat® 2001 (Sn oxalate: 0.1% by weight, based on the composition as a whole). After the separation of water had stopped, the crude product was distilled in an oil pump vacuum through a 250 mm Vigreux column (T=92-94° C.). 282.4 g of a colorless oil were obtained: OHV=<1, AV=<0.1.

Example 1b

Production of a Composition Containing 2-propylheptyl Caprylate, 4-methyl-2-propylhexyl Caprylate and 5-methyl-2-propylhexyl Caprylate by Esterification 158.3 g of a mixture containing 2-propylheptanol (86%), 4-methyl-2-propylhexanol (6%) and 5-methyl-2-propylhexanol (8%) (1 mol) and 144.2 g caprylic acid (1 mol) were heated for 5 h to 220° C. on a water separator together with 0.30 g Fascat® 2001 (Sn oxalate: 0.1% by weight, based on the composition as a whole). After the separation of water had stopped, the crude product was distilled in an oil pump vacuum through a 250 mm Vigreux column (T=92-94° C.). 282.4 g of a colorless oil were obtained: OHV=<1, AV=<0.1.

Example 2a

Production of 2-propylheptyl Caproate by Esterification 158.3 g 2-propylheptanol (1 mol) and 116.2 g caproic acid (1 mol) were heated for 4 h to 220° C. on a water separator together with 0.27 g Fascat® 2001 (Sn oxalate: 0.1% by weight, based on the composition as a whole). After the separation of water had stopped, the crude product was distilled in an oil pump vacuum through a 250 mm Vigreux column (T=111-126° C.). 251.4 g of a colorless oil were obtained: OHV=<1, AV=<0.1.

Example 2b

Production of a Composition Containing 2-propylheptyl Caproate, 4-methyl-2-propylhexyl Caproate and 5-methyl-2-propylhexyl Caproate by Esterification 158.3 g of a mixture containing 2-propylheptanol (86%), 4-methyl-2-propylhexanol (6%) and 5-methyl-2-propylhexanol (8%) (1 mol) and 116.2 g caproic acid (1 mol) were heated for 4 h to 220° C. on a water separator together with 0.27 g Fascat® 2001 (Sn oxalate: 0.1% by weight, based on the composition as a whole). After the separation of water had stopped, the crude product was distilled in an oil pump vacuum through a 250 mm Vigreux column (T=111-126° C.). 251.4 g of a colorless oil were obtained: OHV=<1, AV=<0.1.

Example 3a

Production of 2-propylheptyl Caprate by Esterification 1108.0 g 2-propylheptanol (7 mol) and 1205.9 g capric acid (7 mol) were heated for 6 h to 220° C. on a water separator together with 0.27 g Fascat® 2001 (Sn oxalate: 0.1% by weight, based on the composition as a whole). After the separation of water had stopped, the crude product was distilled in an oil pump vacuum through a 250 mm Vigreux column (T=141-152° C.). 1840.1 g of a colorless oil were obtained: OHV=<0.08, AV=<0.18.

Example 3b

Production of a Composition Containing 2-propylheptyl Caprate, 4-methyl-2-propylhexyl Caprate and 5-methyl-2-propylhexyl Caprate by Esterification 1108.0 g of a mixture containing 2-propylheptanol (86%), 4-methyl-2-propylhexanol (6%) and 5-methyl-2-propylhexanol (8%) (7 mol) and 1205.9 g capric acid (7 mol) were heated for 6 h to 220° C. on a water separator together with 0.27 g Fascat® 2001 (Sn oxalate: 0.1% by weight, based on the composition as a whole). After the separation of water had stopped, the crude product was distilled in an oil pump vacuum through a 250 mm Vigreux column (T=141-152° C.). 1840.1 g of a colorless oil were obtained: OHV=<0.08, AV=<0.18.

Example 4a

Production of a 2-propylheptyl Ester Mixture by Transesterification 1715 g (10 mol) of a technical mixture of hexanoic acid methyl ester, octanoic acid methyl ester and decanoic acid methyl ester (Edenor ME C6-10), 1740 g (11 mol) 2-propylheptanol and 3.6 g tetrabutyl titanate were heated under nitrogen to 200° C. on a water separator. After seven hours, the reaction was terminated. The product was distilled (boiling range: 160-175° C. at 1 mbar) and accumulated as a colorless oil.

Example 4b

Production of a Composition Containing a 2-propylheptyl Ester Mixture, a 4-methyl-2-propylhexyl Ester Mixture and a 5-methyl-2-propylhexyl Ester Mixture by Transesterification 1715 g (10 mol) of a technical mixture of hexanoic acid methyl ester, octanoic acid methyl ester and decanoic acid methyl ester (Edenor ME C6-10), 1740 g (11 mol) of a mixture containing 2-propylheptanol (86%), 4-methyl-2-propylhexanol (6%) and 5-methyl-2-propylhexanol (8%) and 3.6 g tetrabutyl titanate were heated under nitrogen to 200° C. on a water separator. After seven hours, the reaction was terminated. The product was distilled (boiling range: 160-175° C. at 1 mbar) and accumulated as a colorless oil.

Example 5a

Production of a 2-propylheptyl Octanoic Acid Ester by Transesterification 633.2 g (4 mol) 2-propylheptanol, 696.2 g (4.4 mol) octanoic acid methyl ester (Edenor ME C8) and 22.55 g NaOCH$_3$ (30% in methanol) were heated under nitrogen to 220° C. on a water separator. After four hours, the reaction was terminated. The product (propylheptylcaprylate=2-propylheptyl octanoate) was distilled (boiling range: 106-110° C. at 0.04 mbar) and accumulated as a colorless oil.

Example 5b

Production of a Composition Containing 2-propylheptyl Ester Octanoic Acid Ester, 4-methyl-2-propylhexyl Octanoic Acid Ester and 5-methyl-2-propylhexyl Octanoic Acid Ester by Transesterification 633.2 g (4 mol) of a mixture containing 2-propylheptanol (86%), 4-methyl-2-propylhexanol (6%) and 5-methyl-2-propylhexanol (8%), 696.2 g (4.4 mol) octanoic acid methyl ester (Edenor ME C8) and 22.55 g NaOCH$_3$ 30% in methanol) were heated under nitrogen to 220° C. on a water separator. After four hours, the reaction was terminated. The product was distilled (boiling range: 106-110° C. at 0.04 mbar) and accumulated as a colorless oil.

Example 6a

Enzyme-Catalyzed Production of 2-propylheptyl Octanoate by Transesterification 500 g 2-propylheptanol, 500 g octanoic acid methyl ester and 50 g Novozym 435 (Novo, Denmark: immobilized lipase—lipase B—from *Candida antarctica*) were heated under nitrogen for 5 h to 45° C. The temperature was then increased to 60° C. and vacuum (20 mbar) was applied. After 48 h under these conditions, the reaction was terminated. After the enzyme had been filtered off, the product accumulated as a colorless oil. Less than 1% of the educts could be detected by GC.

Example 6b

Enzyme-Catalyzed Production of a Composition Containing 2-propylheptyl Octanoic Acid Ester, 4-methyl-2-propylhexyl Octanoic Acid Ester and 5-methyl-2-propylhexyl Octanoic Acid Ester by Transesterification 500 g of a mixture containing 2-propylheptanol (86%), 4-methyl-2-propylhexanol (6%) and 5-methyl-2-propylhexanol (8%), 500 g octanoic acid methyl ester and 50 g Novozym 435 (Novo, Denmark: immobilized lipase—lipase B—from *Candida antarctica*) were heated under nitrogen for 5 h to 45° C. The temperature was then increased to 60° C. and vacuum (20 mbar) was applied. After 48 h under these conditions, the reaction was terminated. After the enzyme had been filtered off, the product accumulated as a colorless oil. Less than 1% of the educts could be detected by GC.

Cosmetic Preparations

All quantitative data in % by weight active substance, based on the preparation as a whole.

All the following Formulation Examples were carried out on the one hand with the corresponding 2-propylheptyl ester—as specified in the Table—and, on the other hand, with compositions containing the 2-propylheptyl ester specified in the Table and the corresponding 4-methyl-2-propylhexyl ester and the corresponding 5-methyl-2-propylhexyl ester. The total percentage content of the methyl-2-propylhexyl ester in the compositions was 14%, the percentage content of the 2-propylheptyl ester was 86%.

TABLE 1

| | Oil-in-water emulsions | | | | |
|---|---|---|---|---|---|
| Ingredients Trade name (INCI) | 1 | 2 | 3 | 4 | 5 |
| Emulgade ® PL 68/50 (Cetearyl Glucoside, Cetearyl Alcohol) | 4.50 | 4.50 | 4.50 | | |
| Eumulgin ® VL75 (Lauryl Glucoside, Polyglyceryl-2 Dipolyhydroxystearate, Glycerin) | | | | 4.50 | 4.50 |
| 2-Propylheptylcaprate | 16.00 | | | 16.00 | |
| 2-Propylheptylcaprylate | | 16.00 | | | 16.00 |
| 2-Propylheptylcaproate | | | 16.00 | | |

TABLE 1-continued

| | Oil-in-water emulsions | | | | |
|---|---|---|---|---|---|
| | 1 | 2 | 3 | 4 | 5 |
| Carbopol ® 980 | | | | 0.30 | 0.30 |
| Lanette ® O | | | | | |
| KOH (20%) | | | | 0.70 | 0.70 |
| Glycerol, 99.5% | 3.00 | 3.00 | 3.00 | 3.00 | 3.00 |
| Formalin sol., 37% | 0.15 | 0.15 | 0.15 | 0.15 | 0.15 |
| Water dist. | to 100 | to 100 | to 100 | to 100 | to 100 |
| pH value | 7.10 | 5.90 | 5.70 | 6.70 | 6.60 |
| Viscosity (TE spindle, 4 r.p.m., Helipath, 20° C.) [Pa · s]: | | | | | |
| Day 1 | 16800 | 16000 | 13600 | 6000 | 4000 |
| 1 week | 18400 | 16000 | 16000 | 6800 | 4400 |
| 4 weeks | 20000 | 15200 | 14400 | 7600 | 5600 |
| 8 weeks | 17600 | 14400 | 12400 | 7600 | 5600 |
| 12 weeks | 18000 | 14000 | 13200 | 8000 | 5200 |
| Stabilities[3)] | | | | | |
| 1 week RT/−5° C./40° C./45° C./50° C. | 1/1/1/1/5 | 1/1/1/5/5 | 1/1/1/5/5 | 1/1/1/1/1 | 1/1/1/1/1 |
| 4 weeks RT/−5° C./40° C./45° C./50° C. | 1/1/1/1/— | 1/1/1/—/— | 1/1/1/—/— | 1/1/1/1/1 | 1/1/1/1/1 |
| 8 weeks RT/−5° C./40° C./45° C./50° C. | 1/1/1/5/— | 1/1/1/—/— | 1/1/1/—/— | 1/1/1/1/1 | 1/1/1/1/1 |
| 12 weeks RT/−5° C./40° C./45° C./50° C. | 1/1/1/—/— | 1/1/1/—/— | 1/1/1/—/— | 1/1/1/1/1 | 1/1/1/1/1 |

TABLE 2

| | Oil-in-water emulsions | | | |
|---|---|---|---|---|
| | 6 | 7 | 8 | 9 |
| Ingredients: trade name (INCI) | | | | |
| Eumulgin ® VL75 (Lauryl Glucoside, Polyglyceryl-2 Dipolyhydroxystearate, Glycerin) | 4.50 | | | |
| Eumulgin ® B2 (Ceteareth-20) | | 2.00 | 2.00 | 2.00 |
| 2-Propylheptylcaprate | | 16.00 | | |
| 2-Propylheptylcaprylate | | | 16.00 | |
| 2-Propylheptylcaproate | 16.00 | | | 16.00 |
| Carbopol ® 980 | 0.30 | | | |
| Lanette ® O | | 5.00 | 5.00 | 5.00 |
| KOH (20%) | 0.70 | | | |
| Glycerol, 99.5% | 3.00 | 3.00 | 3.00 | 3.00 |
| Formalin sol., 37% | 0.15 | 0.15 | 0.15 | 0.15 |
| Water dist. | to 100 | to 100 | to 100 | to 100 |
| pH value | 6.70 | 7.10 | 5.70 | 6.80 |
| Viscosity (TE spindle, 4 r.p.m., Helipath, 20° C.) [Pa · s]: | | | | |
| Day 1 | 4000 | 11600 | 8800 | 4000 |
| 1 week | 4000 | 13200 | 7200 | 6400 |
| 4 weeks | 4400 | 13600 | 7200 | 8400 |
| 8 weeks | 4800 | 14800 | 6000 | 8400 |
| 12 weeks | 4800 | 14400 | 6000 | 9200 |
| Stabilities[3)] | | | | |
| 1 week RT/−5° C./40° C./45° C./50° C. | 1/1/1/1/1 | 1/1/1/5/5 | 1/1/1/5/5 | 1/5/5/5/5 |
| 4 weeks RT/−5° C./40° C./45° C./50° C. | 1/1/1/1/1 | 1/1/1/—/— | 1/1/1/—/— | 1/1/—/—/— |
| 8 weeks RT/−5° C./40° C./45° C./50° C. | 1/1/1/1/1 | 1/1/1/—/— | 1/1/5/—/— | 1/1/—/—/— |
| 12 weeks RT/−5° C./40° C./45° C./50° C. | 1/1/1/1/1 | 1/1/1/—/— | 1/1/5/—/— | 1/1/—/—/— |

TABLE 3

| | Water-in-oil emulsions | | | | | |
|---|---|---|---|---|---|---|
| | 10 | 11 | 12 | 13 | 14 | 15 |
| Ingredients: Trade name (INCI) | | | | | | |
| Dehymuls ® LE (PEG-30-Dipolyhydroxystearate) | 5.00 | 5.00 | 5.00 | | | |

TABLE 3-continued

| | Water-in-oil emulsions | | | | | |
|---|---|---|---|---|---|---|
| | 10 | 11 | 12 | 13 | 14 | 15 |
| Dehymuls ® PGPH (Polyglyceryl-2-Dipolyhydroxy-stearate) | | | | 4.00 | 4.00 | 4.00 |
| Lameform ® TGI (Polyglyceryl-3-Diisostearate) | | | | 2.00 | 2.00 | 2.00 |
| 2-Propylheptyldecanoate | 20.00 | | | 20.00 | | |
| 2-Propylheptyloctanoate | | 20.00 | | | 20.00 | |
| 2-Propylheptylhexanoate | | | 20.00 | | | 20.00 |
| MgSO4*7H2O | 1.00 | 1.00 | 1.00 | 1.00 | 1.00 | 1.00 |
| Glycerol, 99.5% | 5.00 | 5.00 | 5.00 | 5.00 | 5.00 | 5.00 |
| Formalin sol., 37% | 0.15 | 0.15 | 0.15 | 0.15 | 0.15 | 0.15 |
| Water dist. | to 100 | to 100 | to 100 | to 100 | to 100 | to 100 |
| Viscosity (Brookfield RVF, TE spindle, 4 r.p.m., 20° C.) [Pa·s]: | | | | | | |
| Day 1 | 6000 | 5200 | 3600 | 16000 | 14400 | 9600 |
| 1 week | 6800 | 6000 | 4000 | 18000 | 16400 | 11200 |
| 4 weeks | 6800 | 6000 | 4000 | 20000 | 19600 | 14400 |
| 8 weeks | 6800 | 5600 | 4000 | 21600 | 21600 | 15200 |
| 12 weeks | 6800 | 5600 | 4000 | 21200 | 22000 | 14800 |
| Stabilities[3)]: | | | | | | |
| 1 week RT/−5° C./40° C./45° C./50° C. | 1/1/1/1/1 | 1/1/1/1/1 | 1/1/1/1/1 | 1/1/1/1/1 | 1/1/1/1/1 | 1/1/1/1/1 |
| 4 weeks RT/−5° C./40° C./45° C./50° C. | 1/1/1/1/1 | 1/1/1/1/1 | 1/1/1/1/1 | 1/1/1/1/1 | 1/1/1/1/1 | 1/1/1/1/1 |
| 8 weeks RT/−5° C./40° C./45° C./50° C. | 1/1/1/1/1 | 1/1/1/1/1 | 1/1/1/1/1 | 1/1/1/1/1 | 1/1/1/1/1 | 1/1/1/1/1 |
| 12 weeks RT/−5° C./40° C./45° C./50° C. | 1/1/1/1/1 | 1/1/1/1/1 | 1/1/1/1/1 | 1/1/1/1/1 | 1/1/1/1/1 | 1/1/1/1/1 |

TABLE 4

| | Water-in-oil emulsions | | |
|---|---|---|---|
| Ingredients Trade name (INCI) | 16 | 17 | 18 |
| Dehymuls ® LE (PEG-30-Dipolyhydroxystearate) | 4.00 | 4.00 | 4.00 |
| Lameform ® TGI (Polyglyceryl-3-Diisostearate) | 2.00 | 2.00 | 2.00 |
| 2-Propylheptyldecanoate | 20.00 | | |
| 2-Propylheptyloctanoate | | 20.00 | |
| 2-Propylheptylhexanoate | | | 20.00 |
| MgSO4*7H2O | 1.00 | 1.00 | 1.00 |
| Glycerol 99.5% | 5.00 | 5.00 | 5.00 |
| Formalin sol. 37% | 0.15 | 0.15 | 0.15 |
| Wasser dist. | to 100 | to 100 | to 100 |
| Viscosity (Brookfield RVF, TE spindle, 4 r.p.m., 20° C.) [Pa s]: | | | |
| Day 1 | 18000 | 16000 | 14000 |
| 1 week | 22400 | 23600 | 17600 |
| 4 weeks | 23200 | 20000 | 17600 |
| 8 weeks | 22800 | 19600 | 16800 |
| 12 weeks | 22800 | 20000 | 16800 |
| Stabilities | | | |
| 1 week RT/−5° C./40° C./50° C. | 1/1/1/1/1 | 1/1/1/1/1 | 1/1/1/1/1 |
| 4 weeks RT/−5° C./40° C./50° C. | 1/1/1/1/1 | 1/1/1/1/1 | 1/1/1/1/1 |
| 8 weeks RT/−5° C./40° C./50° C. | 1/1/1/1/1 | 1/1/1/1/1 | 1/1/1/1/1 |
| 12 weeks RT/−5° C./40° C./50° C. | 1/1/1/1/1 | 1/1/1/1/1 | 1/1/1/1/1 |

OTHER FORMULATION EXAMPLES

Example 19

Hair Conditioner

EXAMPLE 19

| Hair Conditioner | |
|---|---|
| Dehyquart ® A CA (Cetrimonium Chloride) | 4.5% |
| Lanette ®O (Cetearyl Alcohol) | 4% |
| Cutina ®CP (Cetyl Palmitate) | 1% |
| 2-Propylheptylcaprylate | 1.5% |
| Eumulgin ®B2 (Ceteareth-20) | 0.3% |
| Preservative | q.s. |
| Aqua demin. | to 100 |

Example 20

Nanoemulsion

EXAMPLE 20

| Nanoemulsion | |
|---|---|
| Monomuls ®90 O 18 (Glyceryl Oleate) | 6.11% |
| 2-Propylheptylcaprylate | 17.88% |
| Eutanol ®G (Octyldodecanol) | 5.97% |
| Plantapon ®LGC Sorb (Sodium Lauryl Glucose Carboxylate (and) Lauryl Glucoside) | 9.5% |
| Plantapon ® ACG 35 (Disodium Cocoyl Glutamate) | 0.78% |
| Phenoxyethanol | 0.5% |
| Phenonip | 0.5% |
| Aqua demin. | to 100 |

TABLE 5

| Trade name (INCI) | 21 | 22 | 23 | V1 | 24 | 25 | 26 | 27 |
|---|---|---|---|---|---|---|---|---|
| Emulgade ® SE-PF (Glyceryl Stearate, Ceteareth-20, Ceteareth-12, Cetearyl Alcohol, Cetyl Palmitate) | 4.80 | | | | | | | |
| Eumulgin ® B2 (Ceteareth-20) | 3.70 | | 3.00 | 3.00 | | | | |
| Emulgade ® PL-68/50 (Cetearyl Glucoside, Cetearyl Alcohol) | | | | | | 5.00 | | |
| Eumulgin ® SG (Sodium Stearoyl Glutamate) | | | | | | 0.50 | 0.20 | |
| Eumulgin ® VL 75 (Lauryl Glucoside, Polyglyceryl-2 Dipolyhydroxystearate, Glycerin) | | 6.00 | | | | | | 0.50 |
| Cutina ® MD (Glyceryl Stearate) | | | | | 2.00 | | | |
| Cutina ® PES (Pentaerythrityl Distearate) | | | | | | | 1.00 | |
| Cetiol ® SenSoft (Propylheptyl Caprylate[1)]) | 5.00 | 7.00 | 2.00 | | 5.00 | 5.00 | 5.00 | 6.00 |
| Cetiol ® 868 (Ethylhexyl Stearate) | | | 7.00 | 7.00 | 4.00 | | | |
| Cetiol ® AB (C12-15 Alkyl Benzoate) | | 7.00 | | | | | | |
| Cetiol ® LC (Coco-Caprylate/Caprate) | | | | | | 5.00 | 5.00 | |
| Myritol ® 331 (Cocoglycerides) | 3.00 | | | | | | | 10.00 |
| Myritol ® 312 (Caprylic/Capric Triglyceride) | | | | | 5.00 | | | |
| Myritol ® 318 (Caprylic/Capric Triglyceride) | | | 7.00 | 7.00 | | | | |
| Dimethicone (Wacker AK 350) | | | | | 0.50 | | | |
| Ethylhexyl Methoxycinnamate (Uvinul MC 80) | 5.00 | 7.50 | | | | | | 7.50 |
| 4-Methylbenzylidene Camphor (Neo Helipan MBC) | 2.00 | | | | | | | |
| Butyl Methoxydibenzoylmethane (Parsol 1789) | 1.50 | 3.50 | | | | | | 2.00 |
| Copherol ® F 1300 C (Tocopherol) | | | | | | 1.00 | | 1.00 |
| Cosmedia ® DC (Hydrogenated Dimer Dilinoleyl/Dimethylcarbonate Copolymer) | | | | | | | | 2.00 |
| Cosmedia ® SP (Sodium Polyacrylate) | | 0.50 | 0.20 | 0.20 | | 1.00 | 1.00 | 0.30 |
| Glycerol | 5.00 | | | | 2.00 | 5.00 | | 5.00 |
| 1,3-Butylene Glycol | | 3.00 | | | 2.00 | | | |
| Phenylbenzimidazole Sulfonic Acid (Neo Heliopan Hydro, 15% aqueous solution) | 13.30 | | | | | | | |
| Methylene Bis-Benzotriazolyl Tetramethylbutylphenol (Tinosorb M) | | 5.00 | | | | | | |
| Tapioca starch | | | | 2.00 | | | | |
| Water, preservative q.s. | | | | | to 100 | | | |
| NaOH (10%) | pH 7.0 | pH 6.6 | pH 6.3 | pH 6.3 | pH 7.0 | pH 6.1 | pH 6.5 | pH 6.0 |
| Viscosity data[2)] at 20° C. [Pa · s] | | | | | | | | |
| after preparation | <400 | <400 | 2000 | 1200 | 87500 | 187500 | 112500 | 12800 |
| after 1 week | <400 | <400 | 2000 | 1200 | 62500 | 162500 | 112500 | 12400 |
| after 2 weeks | <400 | <400 | 2400 | 1200 | 62500 | 162500 | 112500 | 11600 |
| after 4 weeks | <400 | | 2400 | 1200 | 62500 | 150000 | | |
| after 8 weeks | <400 | | 2800 | 1600 | 62500 | 162500 | | |
| Phase stability[3)] at −5° C./20° C./40° C. | | | | | | | | |
| after 1 week | 1/1/1 | 1/1/1 | 1/1/1 | 1/1/1 | 1/1/1 | 1/1/1 | 1/1/1 | 1/1/1 |
| after 2 weeks | 1/1/1 | 1/1/1 | 1/1/1 | 1/1/1 | 1/1/1 | 1/1/1 | 1/1/1 | 1/1/1 |
| after 4 weeks | 1/1/1 | | 1/1/1 | 1/1/1 | 1/1/1 | 1/1/1 | | |
| after 8 weeks | 1/1/1 | | 1/1/5 | 1/1/1 | 1/1/1 | 1/1/1 | | |
| Macroscopic[4)]/microscopic[5)] appearance at 20° C. | —/1 | 2/2 | 2/2 | 2/2 | 2/3 | 2/2 | 2/3 | 1/3 |
| Sensory evaluation[6)] | | | | | | | | |
| softness | 1 | 1 | 1 | 3 | 1 | 1 | 1 | 1 |
| smoothness | 1 | 1 | 2 | 1 | 2 | 1 | 1 | 2 |

TABLE 6

| Trade name (INCI) | 28 | 29 | 30 | 31 |
|---|---|---|---|---|
| Dehymuls ® PGPH (Polyglyceryl-2 Dipolyhydroxystearate) | 2.00 | 2.00 | | |
| Dehymuls ® LE (PEG-30 Dipolyhydroxystearate) | | 2.00 | | |
| Cyclopentasiloxane, Caprylyl Dimethicone, Ethoxy Glucoside (Wacker Belsil SPG 128 VP) | 12.00 | | | |

TABLE 6-continued

|  | 28 | 29 | 30 | 31 |
|---|---|---|---|---|
| Beeswax 8100 (Kahl) | 1.00 | | | |
| Zinc stearate (Zinkum N 29) | 1.00 | | | |
| Texapon ® NSO (Sodium Laureth Sulfate) | | | | 34.00 |
| Dehyton ® PK 45 (Cocamidopropyl Betaine) | | | | 8.00 |
| Emulgade ® NLB (Steareth-2, Ceteareth-12, Stearyl Alcohol, Ceteareth-20, Distearyl Ether) | | | | 3.00 |
| Polyquaternium-10 (Polymer JR 400) | | | | 0.20 |
| Acrylates Copolymer (Carbopol Aqua SF-1) | | | | 8.00 |
| Cetiol ® SenSoft (Propylheptyl Caprylate[1]) | 8.00 | 6.00 | 10.00 | 3.00 |
| Cetiol ® 868 (Ethylhexyl Stearate) | 7.00 | | | |
| Cetiol ® A (Hexyl Laurate) | | 6.00 | | |
| Cetiol ® SN (Cetearyl Isononanoate) | | 7.00 | | |
| Eutanol ® G 16 (Hexyldecanol) | | 3.00 | | |
| Myritol ® 331 (Cocoglycerides) | | | 31.00 | |
| Helianthus Annuus (sunflower oil) | | | 57.00 | |
| Copherol ® 1250 C (Tocopheryl Acetate) | | | 1.00 | |
| Copherol ® F 1300 C (Tocopherol) | 1.00 | | | |
| Glycerol | | 5.00 | | |
| 1,3-Butylene Glycol | 3.00 | | | |
| Sodium Chloride | 0.40 | | | |
| Magnesium Sulfate Heptahydrate | | 1.00 | | |
| Alcohol (Ethanol) | | 4.00 | | |
| Hydagen ® B (Bisabolol) | | | 0.50 | |
| Water, preservative q.s. | to 100 | to 100 | | to 100 |
| Viscosity data[2] at 20° C. [Pa · s] | | | | |
| after preparation | 11200 | 2400 | <400 | 3000 |
| after 1 week | 20000 | 2400 | <400 | 3400 |
| after 2 weeks | 20000 | 2400 | <400 | 3400 |
| after 4 weeks | 20000 | | <400 | 3600 |
| after 8 weeks | 19600 | | | |
| Phase stability[3] at −5° C./20° C./40° C. | | | | |
| after 1 week | 1/1/1 | 1/1/1 | 1/1/1 | 1/1/1 |
| after 2 weeks | 1/1/1 | 1/1/1 | 1/1/1 | 1/1/1 |
| after 4 weeks | 1/1/1 | | 1/1/1 | 1/1/1 |
| after 8 weeks | 1/1/1 | | | |
| Macroscopic[4]/microscopic[5] appearance at 20° C. | 1/2 | 1/1 | n.d. | n.d. |
| Sensory evaluation[6] | | | | |
| softness | 1 | 1 | 1 | 1 |
| smoothness | 1 | 1 | 1 | 1 |

TABLE 7

|  | 32 | 33 | 34 |
|---|---|---|---|
| Trade name (INCI) | | | |
| Emulgade ® NLB (Steareth-2, Ceteareth-12, Stearyl Alcohol, Ceteareth-20, Distearyl Ether) | 5.00 | 5.00 | |
| Lanette ® 18 (Stearyl Alcohol) | | | 14.70 |
| Cutina ® HR (Hydrogenated Castor Oil) | | | 3.70 |
| Cetiol ® SenSoft (Propylheptyl Caprylate[1]) | 6.00 | 4.50 | 23.70 |
| Cyclomethicone (Dow Corning 245) | | 1.50 | 35.00 |
| Aluminium Chlorohydrate (Chlorhydrol 50%) | 40.00 | 20.00 | |
| Aluminium Zirconium Tetrachlorohydrex GLY (Rezal 36 GP) | | | 22.90 |
| Water | to 100 | to 100 | |
| Viscosity data[2] at 20° C. [Pa · s] | | | |
| after preparation | <400 | 440 | |
| after 1 week | 2000 | 5600 | |
| after 2 weeks | 2000 | 5200 | |
| after 4 weeks | 2800 | 4800 | |
| after 8 weeks | 2800 | 4800 | |
| after 12 weeks | 3200 | | |
| Hardness | | | |
| after 1 day | | | 3.3 |
| after 12 weeks | | | 3.5 |
| Phase stability[3] at −5° C./20° C./40° C. | | | |
| aftere 1 week | 1/1/1 | 1/1/1 | 1/1/1 |
| after 2 weeks | 1/1/1 | 1/1/1 | |
| after 4 weeks | 1/1/1 | 1/1/1 | 1/1/1 |
| after 8 weeks | 1/1/2 | 1/1/1 | 1/1/1 |
| after 12 weeks | 1/1/2 | | 1/1/1 |
| Macroscopic[4]/microscopic[5] appearance at 20° C. | 2/1 | 2/2 | n.a. |

Footnotes to the Tables:

RT = room temperature 20° C.; r.p.m. = revolutions per minute

[1]Proposed INCI

[2]Viscosity measurements: Brookfield RVF, spindle 5, 10 revolutions per minute, 23° C. (formulations 21, 22, 23, C1 and 27, 28 to 34) or Brookfield RVF, spindle TE with Helipath, 4 revolutions per minute, 23° C. (formulations 24, 25 and 26)

[3]Evaluation criteria for visual phase stability: 1 = stable; 2 = slight separations; 3 = separations; 4 = distinct separations; 5 = separations

[4]Evaluation criteria for visual macroscopic appearance: 1 = smooth and sparkling; 2 = smooth and flat; 3 = flat/coarse structure; 4 = visible recrystallizates. The formulations were evaluated after thermostatting to RT.

[5]Evaluation criteria for microscopic appearance: 1 = mean particle size ≤ 1 μm; 2 = mean particle size 1-4 μm; 3 = mean particle size 4-13 μm; 4 = mean particle size 13-20 μm; 5 = mean particle size 20-50 μm. The particle size of the test emulsion was visually compared with the particle size of standard emulsions. To determine the particle size of the standard emulsions, a diffraction pattern is produced by laser diffraction. The particle size distribution is then calculated from the light intensities of these diffraction patterns using the Fraunhofer theory (Sympatec Helos).

[6]Sensory evaluation criteria:

The sensory evaluation was carried out as follows:

Test group: 10 experienced and trained volunteers; 1 = very high acceptance; 2 = average acceptance; 3 = unacceptable 10 μl of the above-mentioned compositions thermostatted beforehand to 20° C. were applied by micropipette to the smooth side of the forearms of the volunteers and rubbed in with the fingers of the hands of the contralateral side. The sensory evaluation was carried out during and after absorption. The sensory test was conducted on 10 volunteers, as described in the book "Cosmetic Lipids and the Skin Barrier" (Marcel Dekker, New York, 2002, Ed. Thomas Förster, pp. 319-352).

We claim:

1. The compound 2-propylheptyl-n-octanoic acid ester.

2. A process for the production of 2-propylheptyl-n-octanoic acid ester in which a mixture comprising 2-propylheptanol and [n-]octanoic acid is reacted.

3. A process for the production of 2-propylheptyl-n-octanoic acid ester wherein a mixture comprising 2-propylheptanol and a methyl ester of n-octanoic acid is reacted in the presence of a transesterification catalyst.

4. A cosmetic composition comprising;
2-propylheptyl-n-octanoic acid ester; and
a cosmetically suitable component selected from an emulsifier, surfactant, wax component, polymer, and oil component.

5. The composition according to claim 4, comprising 0.1 to 80%, by weight, 2-propylheptyl-n-octanoic acid ester.

6. The composition according to claim 4, comprising 0.1 to 70%, by weight, 2-propylheptyl-n-octanoic acid ester.

7. The composition according to claim 4, comprising 0.1 to 60%, by weight, 2-propylheptyl-n-octanoic acid ester.

8. The composition according to claim 4, comprising 0.1 to 50%, by weight, 2-propylheptyl-n-octanoic acid ester.

9. The composition according to claim 4, comprising 0.1 to 40%, by weight, 2-propylheptyl-n-octanoic acid ester.

10. A cosmetic composition according to claim 4 additionally comprising one or more members of the group consisting of one or more emulsifiers, one or more surfactants, one or more wax components, one or more polymers, one or more other oil components and mixtures of two or more thereof.

11. The compositions according to claim 10 comprising:
 a) 0.1 to 80%, by weight 2-propylheptyl-n-octanoic acid ester;
 b) 0.1 to 20%, by weight in the aggregate, of one or more members of the group consisting of one or more emulsifiers, one or more surfactants, one or more wax components and one or more polymers;
 c) 0.1 to 40% by weight in the aggregate, of one or more other oil components; and additionally 0 to 98%, by weight, of water.

\* \* \* \* \*